United States Patent
Cummings et al.

(10) Patent No.: US 8,834,466 B2
(45) Date of Patent: Sep. 16, 2014

(54) SURGICAL INSTRUMENT COMPRISING AN ARTICULATABLE END EFFECTOR

(75) Inventors: John F. Cummings, Madeira, OH (US); Andrew T. Beckman, Cincinnati, OH (US); Cory G. Kimball, Cincinnati, OH (US); Al Mirel, Redwood City, CA (US); Christopher J. Schall, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1075 days.

(21) Appl. No.: 12/832,361

(22) Filed: Jul. 8, 2010

(65) Prior Publication Data

US 2012/0010615 A1    Jan. 12, 2012

(51) Int. Cl.
*A61B 18/12*    (2006.01)

(52) U.S. Cl.
USPC .............................. 606/51; 606/52

(58) Field of Classification Search
CPC ............ A61B 18/085; A61B 18/1442; A61B 18/1445; A61B 2018/1442; A61B 2018/1445; A61B 2018/1455; A61B 2018/0225; A61B 17/28–17/29
USPC ............................. 606/51–52, 169, 205–207; 607/101–102; 600/137, 142
See application file for complete search history.

(56) References Cited

U.S. PATENT DOCUMENTS

| | | | |
|---|---|---|---|
| 3,580,841 A | 5/1971 | Cadotte et al. | |
| 3,703,651 A | 11/1972 | Blowers | |
| 4,058,126 A | 11/1977 | Leveen | |
| 4,237,441 A | 12/1980 | van Konynenburg et al. | |
| 4,304,987 A | 12/1981 | van Konynenburg | |
| 4,545,926 A | 10/1985 | Fouts, Jr. et al. | |
| 4,849,133 A | 7/1989 | Yoshida et al. | |
| 4,910,389 A | 3/1990 | Sherman et al. | |

(Continued)

FOREIGN PATENT DOCUMENTS

| | | |
|---|---|---|
| EP | 1749479 A1 | 2/2007 |
| EP | 1915953 A1 | 4/2008 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Michael Peffley
*Assistant Examiner* — Khadijeh Vahdat

(57) ABSTRACT

A surgical instrument can comprise a handle and an end effector, wherein the end effector can comprise first and second jaws which can be opened and closed in order to capture tissue therebetween. The surgical instrument can further comprise a shaft extending between the handle and the effector and means for articulating the end effector relative to the shaft. The articulating means can comprise a portion of the shaft which is rotatable about a first axis in order to articulate the end effector about a second axis. In at least one embodiment, the shaft can comprise a first portion including a cam and a second portion including a cam follower, wherein the rotation of the second portion and the interaction of the cam and cam follower can cause the second portion to pivot relative to the first portion.

19 Claims, 27 Drawing Sheets

(56) References Cited

U.S. PATENT DOCUMENTS

| | | |
|---|---|---|
| 5,104,025 A | 4/1992 | Main et al. |
| 5,106,538 A | 4/1992 | Barma et al. |
| 5,108,383 A | 4/1992 | White |
| 5,205,459 A | 4/1993 | Brinkerhoff et al. |
| 5,285,945 A | 2/1994 | Brinkerhoff et al. |
| 5,309,927 A | 5/1994 | Welch |
| 5,387,207 A | 2/1995 | Dyer et al. |
| 5,403,312 A | 4/1995 | Yates et al. |
| 5,428,504 A | 6/1995 | Bhatla |
| 5,504,650 A | 4/1996 | Katsui et al. |
| 5,511,556 A | 4/1996 | DeSantis |
| 5,563,179 A | 10/1996 | Stone et al. |
| 5,624,452 A | 4/1997 | Yates |
| 5,647,871 A | 7/1997 | Levine et al. |
| 5,716,366 A | 2/1998 | Yates |
| 5,762,255 A | 6/1998 | Chrisman et al. |
| 5,817,033 A | 10/1998 | DeSantis et al. |
| 5,880,668 A | 3/1999 | Hall |
| 6,063,098 A * | 5/2000 | Houser et al. .......... 606/169 |
| 6,074,389 A | 6/2000 | Levine et al. |
| 6,292,700 B1 | 9/2001 | Morrison et al. |
| 6,340,878 B1 | 1/2002 | Oglesbee |
| 6,500,176 B1 | 12/2002 | Truckai et al. |
| 6,503,248 B1 | 1/2003 | Levine |
| 6,533,784 B2 | 3/2003 | Truckai et al. |
| 6,575,969 B1 | 6/2003 | Rittman, III et al. |
| 6,589,200 B1 | 7/2003 | Schwemberger et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,802,843 B2 | 10/2004 | Truckai et al. |
| 6,811,842 B1 | 11/2004 | Ehrnsperger et al. |
| 6,905,497 B2 | 6/2005 | Truckai et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,055,731 B2 | 6/2006 | Shelton, IV et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,404,508 B2 | 7/2008 | Smith et al. |
| 7,435,582 B2 | 10/2008 | Zimmermann et al. |
| 7,464,846 B2 | 12/2008 | Shelton, IV et al. |
| 7,510,107 B2 | 3/2009 | Timm et al. |
| 7,513,025 B2 | 4/2009 | Fischer |
| 7,540,872 B2 | 6/2009 | Schechter et al. |
| 7,550,216 B2 | 6/2009 | Ofer et al. |
| 7,588,176 B2 | 9/2009 | Timm et al. |
| 7,641,671 B2 | 1/2010 | Crainich |
| 7,665,647 B2 | 2/2010 | Shelton, IV et al. |
| 7,708,751 B2 | 5/2010 | Hughes et al. |
| 7,753,904 B2 | 7/2010 | Shelton, IV et al. |
| 7,784,663 B2 | 8/2010 | Shelton, IV |
| 7,819,298 B2 | 10/2010 | Hall et al. |
| 7,832,612 B2 | 11/2010 | Baxter, III et al. |
| 7,879,070 B2 * | 2/2011 | Ortiz et al. .......... 606/205 |
| 2003/0114851 A1 | 6/2003 | Truckai et al. |
| 2004/0232196 A1 | 11/2004 | Shelton, IV et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0138003 A1 | 5/2009 | Deville et al. |
| 2009/0206140 A1 | 8/2009 | Scheib et al. |
| 2009/0209979 A1 | 8/2009 | Yates et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2012/0010616 A1 | 1/2012 | Huang et al. |

FOREIGN PATENT DOCUMENTS

| | | |
|---|---|---|
| WO | WO 03/030708 A2 | 4/2003 |
| WO | WO 2005/052959 A2 | 6/2005 |
| WO | WO 2008/020964 A2 | 2/2008 |
| WO | WO 2009/149234 A1 | 12/2009 |

OTHER PUBLICATIONS

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

(56) References Cited

OTHER PUBLICATIONS

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979).

International Search Report for PCT/US2011/043008, Jul. 6, 2012 (8 pages).

\* cited by examiner

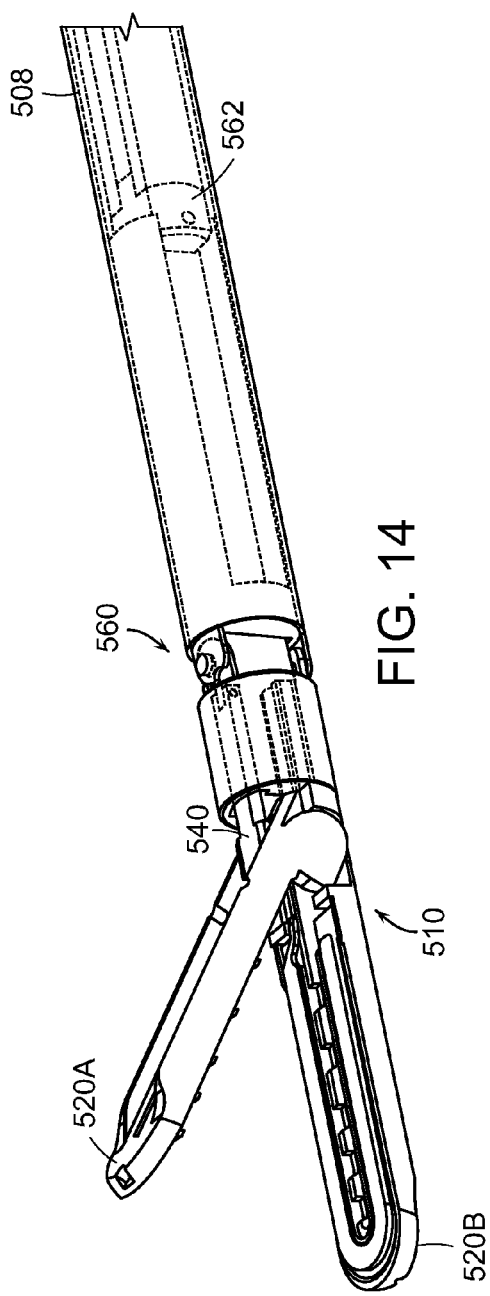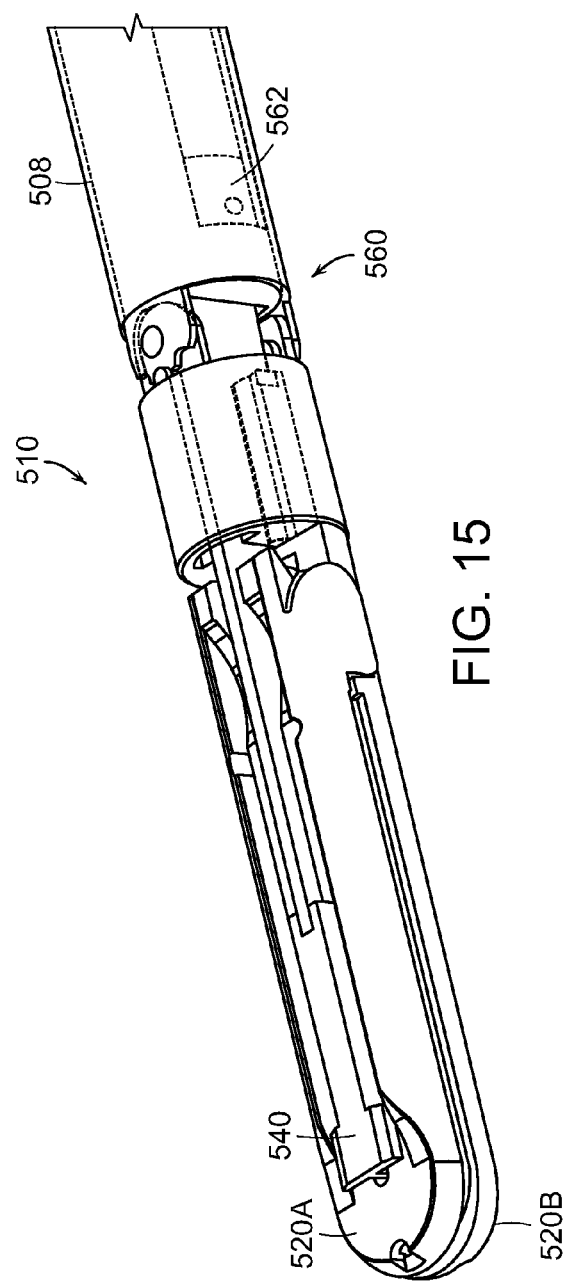

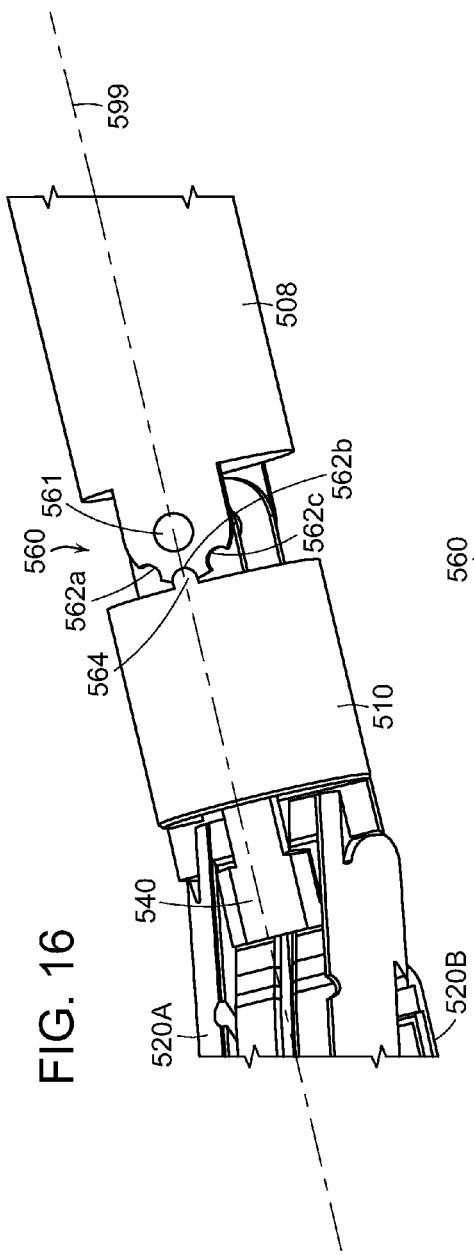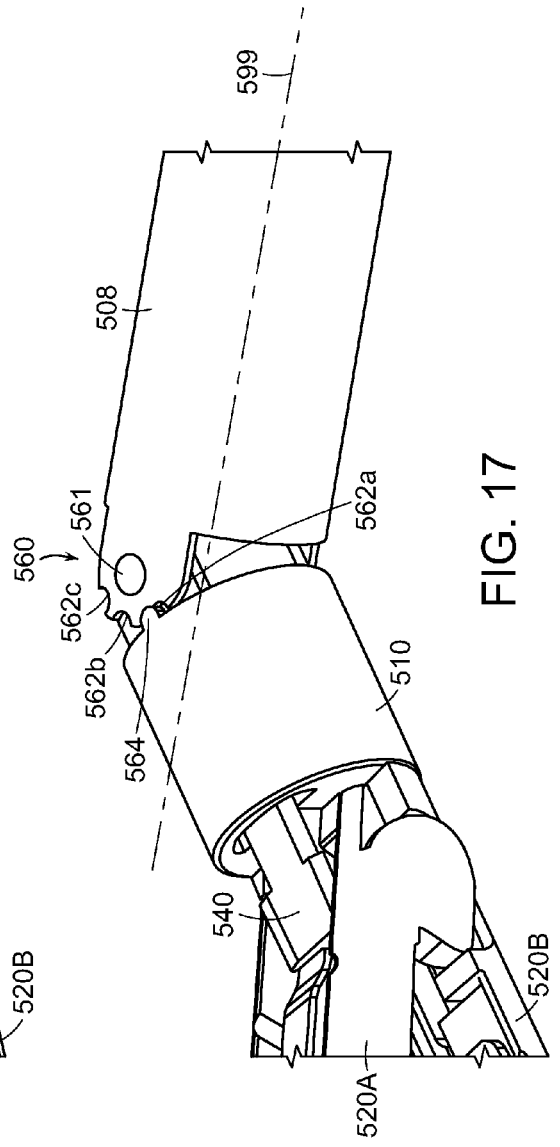

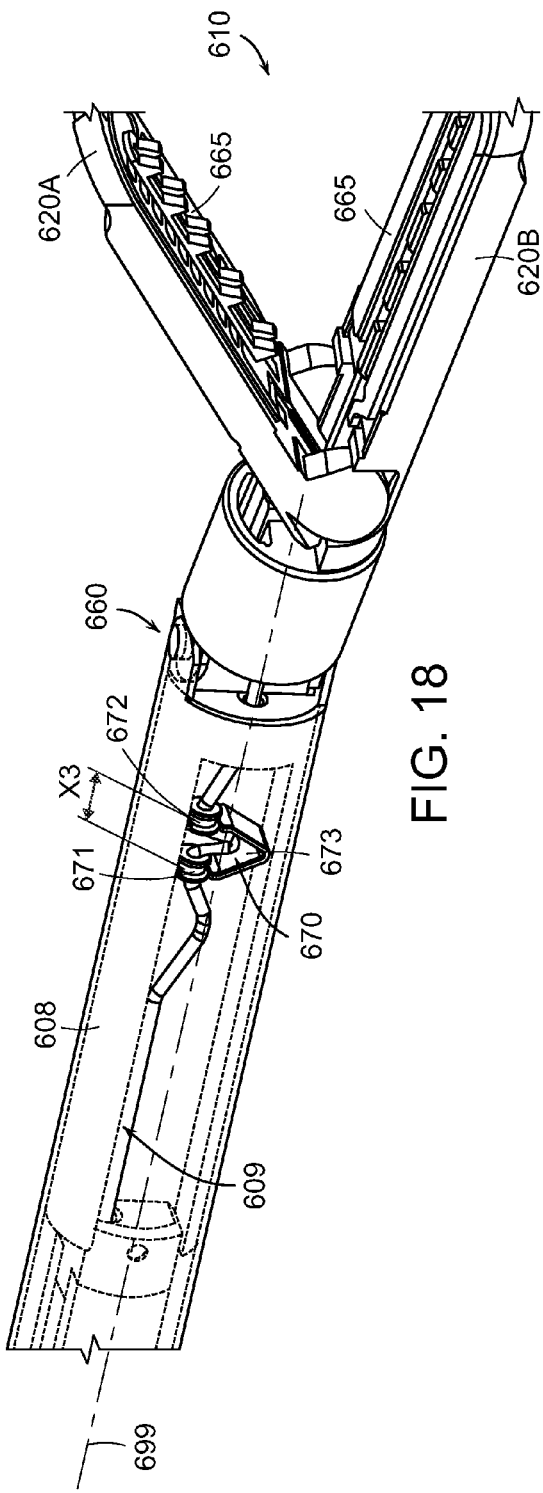
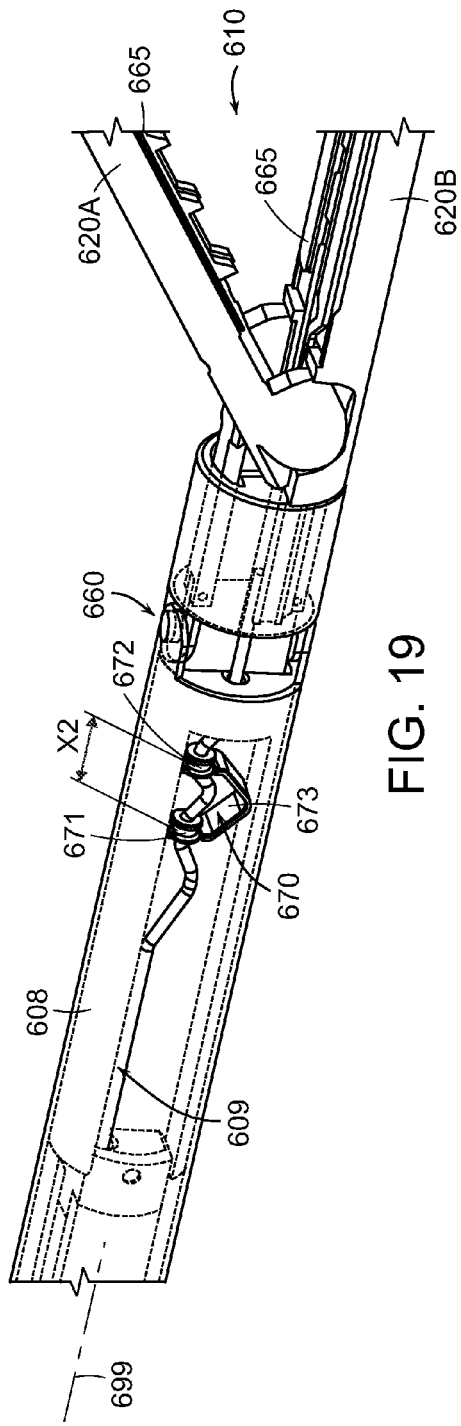
FIG. 18
FIG. 19

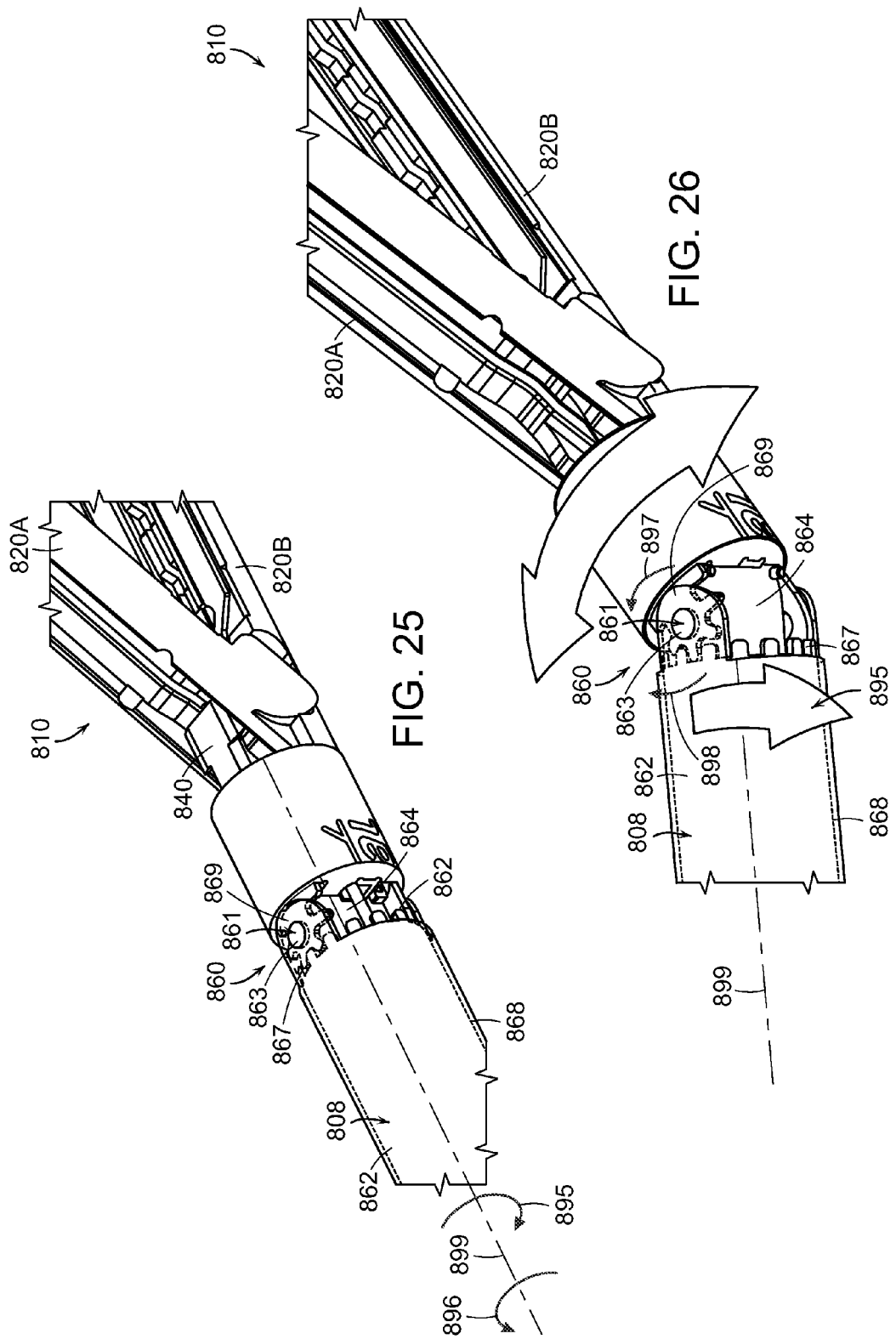

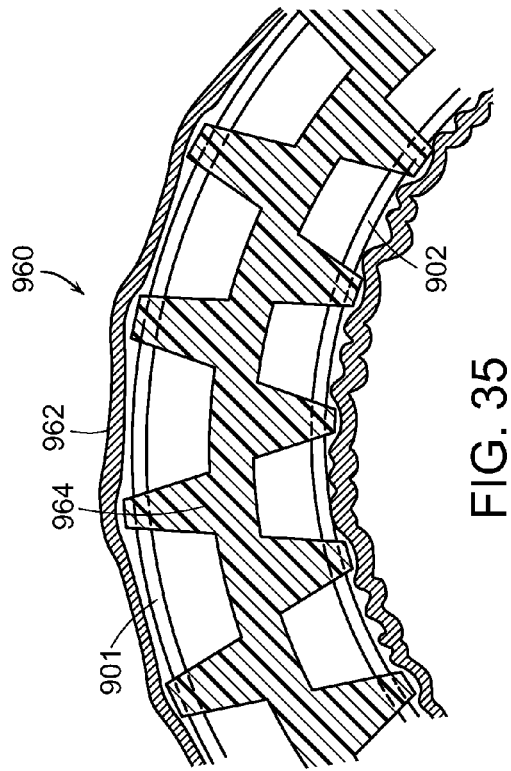
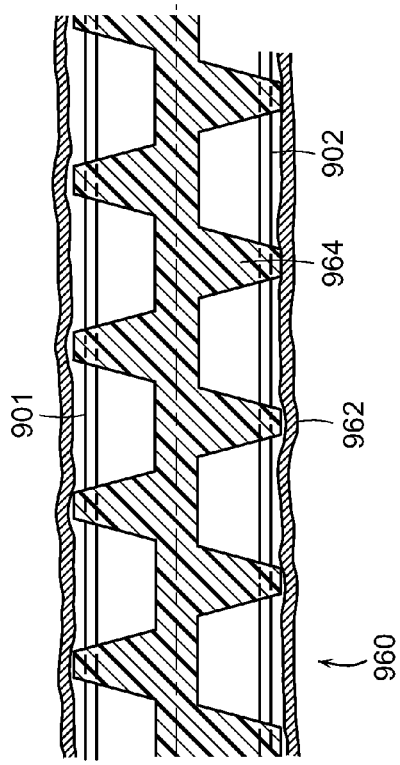
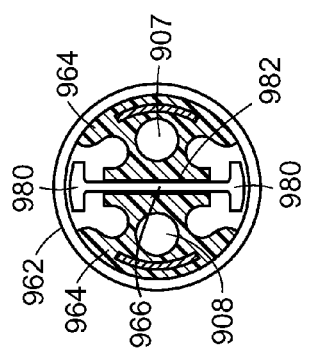
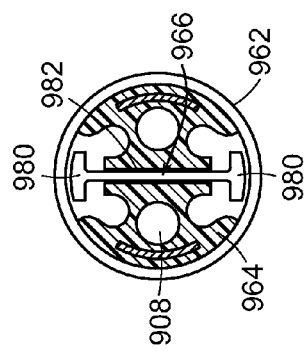
FIG. 35
FIG. 33
FIG. 36
FIG. 34

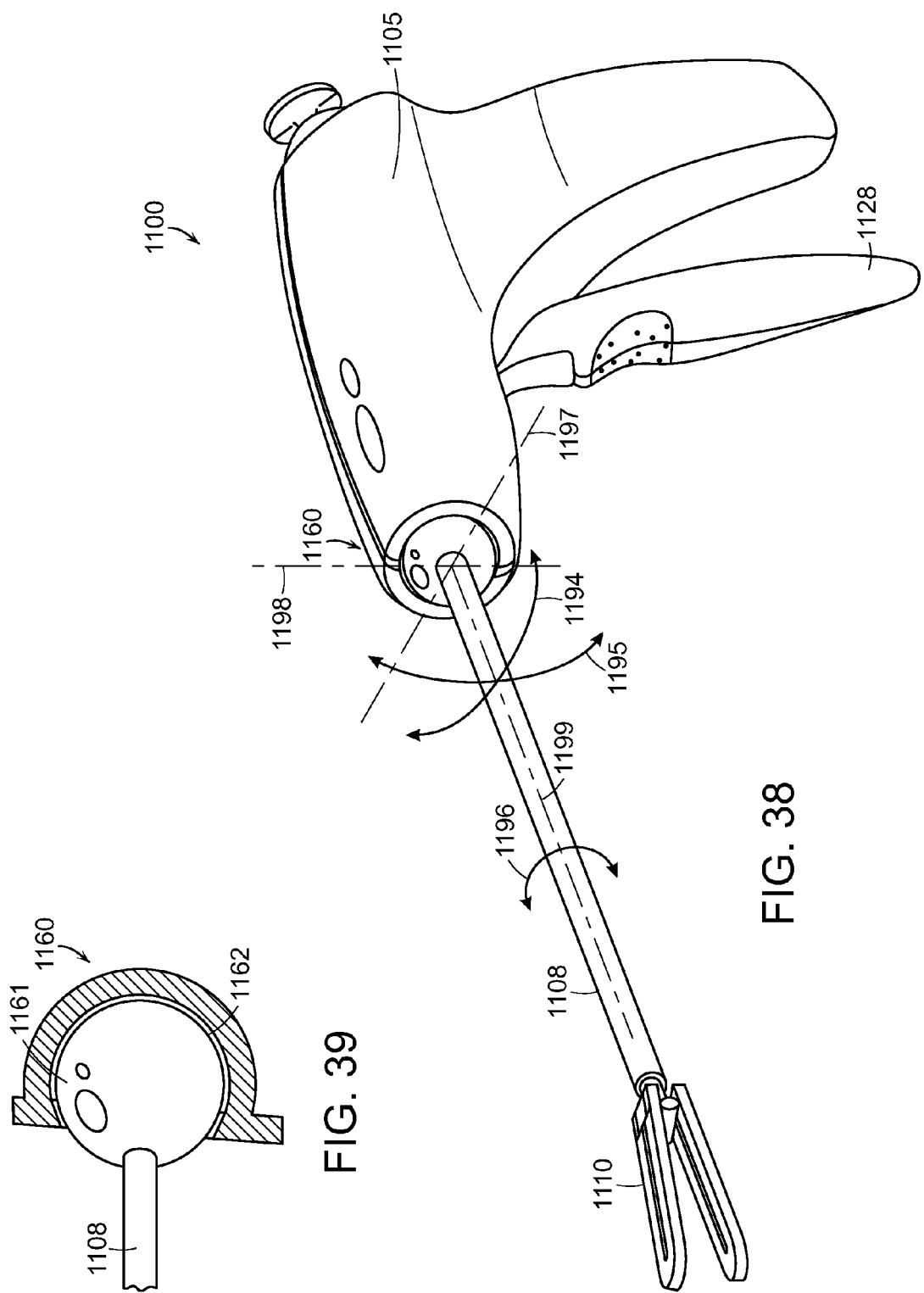

SURGICAL INSTRUMENT COMPRISING AN ARTICULATABLE END EFFECTOR

BACKGROUND

1. Field of the Invention

The present invention relates to medical devices and methods. More particularly, the present invention relates to electrosurgical instruments and methods for sealing and transecting tissue.

2. Description of the Related Art

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (RF) surgical instruments and surgical techniques have been developed for such purposes. In general, the delivery of RF energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radiofrequency (RF) surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In at least one form, a surgical instrument can comprise a handle, a first conductor, a second conductor, and an end effector comprising a first jaw and a second jaw, wherein one of the first jaw and the second jaw is movable relative to the other of the first jaw and the second jaw between an open position and a closed position. The end effector can further comprise a first electrode electrically coupled with the first conductor, and a second electrode electrically coupled with the second conductor, the second electrode comprising a porous material, and an evaporable material stored within the porous material.

In at least one form, a surgical instrument can comprise a handle, a first conductor, a second conductor electrically engageable with a power source, and an end effector comprising a first jaw and a second jaw, wherein one of the first jaw and the second jaw is movable relative to the other of the first jaw and the second jaw between an open position and a closed position. The end effector can further comprise a first electrode electrically coupled with the first conductor, and a second electrode electrically coupled with the second conductor, wherein the second electrode comprises a first material comprised of an electrically non-conductive material and a second material comprised of an electrically conductive material, and wherein the second material is interdispersed within the first material when the second electrode is below a switching temperature. The second material is configured to withdraw from the first material when the temperature of the second material at least one of meets or exceeds the switching temperature.

In at least one form, an end effector for use with a surgical instrument can comprise a first conductor, a second conductor, a first jaw, and a second jaw, wherein one of the first jaw and the second jaw is movable relative to the other of the first jaw and the second jaw between an open position and a closed position. The end effector can further comprise a first electrode electrically coupled with the first conductor and a second electrode electrically coupled with the second conductor, the second electrode comprising a porous material and an evaporable material stored within the porous material.

In at least one form, a surgical instrument can comprise a first jaw comprising an electrode, a second jaw, and a control circuit, wherein the control circuit can comprise a supply conductor configured to be placed in electrical communication with a positive terminal of a power source, a temperature sensor, and a field effect transistor. The field effect transistor can comprise a source terminal in electrical communication with the supply conductor, a drain terminal in electrical communication with the electrode, a gate terminal in electrical communication with the temperature sensor, and a channel comprising a semiconductor material in electrical communication with the source terminal and the drain terminal.

In at least one form, a surgical instrument can comprise a handle comprising a trigger, a shaft comprising a proximal shaft portion coupled to the handle and a distal shaft portion, and an articulation joint connected to the distal shaft portion. The surgical instrument can further comprise an end effector including a proximal end coupled to the articulation joint, a distal end, a first jaw member, a second jaw member, wherein one of the first jaw member and the second jaw member is movable relative to the other of the first jaw member and the second jaw member, and an electrode. The surgical instrument can further comprise a drive member extending through the articulation joint, wherein the drive member is operably coupled with the trigger, wherein an actuation of the trigger is configured to move the drive member toward the distal end of the end effector, wherein the drive member comprises a first flexible layer and a second flexible layer, wherein the first flexible layer is comprised of an electrically conductive material, and wherein the second flexible layer is comprised of an electrically insulative material.

In at least one form, a surgical instrument can comprise a handle comprising a trigger and, in addition, a shaft comprising a proximal shaft portion coupled to the handle, a distal shaft portion, and an articulation joint rotatably connecting the proximal shaft portion and the distal shaft portion, wherein one of the proximal shaft portion and the distal shaft portion comprises a detent, wherein the other of the proximal shaft portion and the distal shaft portion comprises a plurality of notches configured to selectively receive the detent, and wherein each notch is configured to removably hold the distal shaft portion at an articulated angle with respect to the proximal shaft portion. The surgical instrument can further comprise an end effector including a proximal end coupled to the distal shaft portion, a distal end, a first jaw member, a second jaw member, wherein one of the first jaw member and the second jaw member is movable relative to the other of the first jaw member and the second jaw member, and an electrode. The surgical instrument can further comprise a drive member extending through the articulation joint of the shaft, wherein the drive member is operably coupled with the trigger, and wherein an actuation of the trigger is configured to move the drive member toward the distal end of the end effector.

In at least one form, a surgical instrument can comprise a handle comprising a trigger, a shaft comprising a proximal shaft portion coupled to the handle and a distal shaft portion, and an articulation joint connected to the distal shaft portion. The surgical instrument can further comprise an end effector coupled to the articulation joint including a first jaw member, a second jaw member, wherein one of the first jaw member and the second jaw member is movable relative to the other of the first jaw member and the second jaw member, and an electrode. The surgical instrument can further comprise a flexible conductor in electrical communication with the electrode, wherein the flexible conductor extends through the shaft and the articulation joint and, in addition, a spring comprising a proximal end mounted to the flexible conductor, a distal end mounted to the flexible conductor, and an intermediate portion connecting the proximal end and the distal end, wherein the intermediate portion extends along the flexible conductor, and wherein the intermediate portion is configured to flex between a first configuration defining a first length between the proximal end and the distal end and a second configuration defining a second length between the proximal end and the distal end. The surgical instrument can further comprise a drive member extending through the articulation joint of the shaft, wherein the drive member is operably coupled with the trigger, and wherein an actuation of the trigger is configured to move the drive member toward the distal end of the end effector.

In at least one form, a surgical instrument can comprise a handle comprising a trigger and an articulation actuator and, in addition, a shaft comprising a proximal shaft portion coupled to the handle, wherein the proximal shaft portion defines a longitudinal axis, an articulation drive member operably coupled with the articulation actuator, wherein the articulation drive member is configured to be rotated about the longitudinal axis by the articulation actuator, and a distal shaft portion rotatably coupled to the proximal shaft portion about a pivot axis, wherein the articulation drive member is operably engaged with the distal shaft portion, and wherein the rotation of the articulation drive member about the longitudinal axis is configured to rotate the distal shaft portion about the pivot axis. The surgical instrument can further comprise an end effector including a proximal end coupled to the distal shaft portion, a distal end, a first jaw member, a second jaw member, wherein one of the first jaw member and the second jaw member is movable relative to the other of the first jaw member and the second jaw member, and an electrode, and, in addition, a drive member extending through the articulation joint of the shaft, wherein the drive member is operably coupled with the trigger, and wherein an actuation of the trigger is configured to move the drive member toward the distal end of the end effector.

In at least one form, a surgical instrument can comprise a handle including a trigger, a shaft, an articulation joint pivotably coupling the handle and the shaft, wherein the handle comprises a socket and the shaft comprises a ball positioned within the socket, and an end effector comprising a proximal end coupled to the shaft, a distal end, a first jaw member, a second jaw member, wherein one of the first jaw member and the second jaw member is movable relative to the other of the first jaw member and the second jaw member, and an electrode. The surgical instrument can further comprise a drive member extending through the articulation joint of the shaft, wherein the drive member is operably coupled with the trigger, wherein an actuation of the trigger is configured to move the drive member toward the distal end of the end effector.

In at least one form, a surgical instrument can comprise a handle comprising a trigger and an articulation actuator, wherein the articulation actuator comprises a first attachment portion and a second attachment portion, a shaft extending from the handle, and an articulation joint connected to the shaft, the articulation joint comprising an outer housing, an elongate aperture extending through the outer housing, and support structures extending inwardly from the outer housing. The surgical instrument can further comprise an end effector including a proximal end coupled to the shaft, a distal end, a first jaw member, a second jaw member, wherein one of the first jaw member and the second jaw member is movable relative to the other of the first jaw member and the second jaw member, an electrode, a first lateral side portion, and a second lateral side portion, a first articulation driver coupled to the first lateral side portion of the end effector and the first attachment portion of the articulation actuator such that the rotation of the articulation actuator in a first direction articulates the end effector toward the first lateral side portion, a second articulation driver coupled to the second lateral side portion of the end effector and the second attachment portion of the articulation actuator such that the rotation of the articulation actuator in a second direction articulates the end effector toward the second lateral side portion; and a drive member extending between the support structures of the articulation joint, wherein the drive member is operably coupled with the trigger, and wherein an actuation of the trigger is configured to move the drive member toward the distal end of the end effector The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 14 is a perspective view of an end effector in an open configuration, a distal end of a shaft of an electrosurgical instrument, and an articulation joint connecting the end effector and the distal end of the shaft.

FIG. 15 is a perspective view of the end effector of FIG. 14 in an open configuration.

FIG. 16 is a perspective view of an articulation joint of an electrosurgical instrument illustrated in an unarticulated configuration.

FIG. 17 is a perspective view of the articulation joint of FIG. 16 in an articulated configuration.

FIG. 18 a perspective view of an end effector of an electrical surgical instrument illustrated in an open configuration, a distal end of a shaft, and an articulation joint connecting the end effector and the distal end of the shaft, wherein the end effector is illustrated as being articulated to a first side.

FIG. 19 is a perspective view of the end effector of FIG. 18 in an unarticulated configuration.

FIG. 25 is a perspective view of an end effector of an electrical surgical instrument illustrated in an open configuration, a distal end of a shaft, and an articulation joint connecting the end effector and the distal end of the shaft, wherein the end effector is illustrated in an unarticulated configuration.

FIG. 26 is a perspective view of the end effector of FIG. 25 illustrated in an articulated configuration.

FIG. 33 is another cross-sectional view of the articulation joint of the electrosurgical instrument of FIG. 27 in an unarticulated configuration.

FIG. 34 is a cross-sectional end view of the articulation joint of the electrosurgical instrument of FIG. 27 in an unarticulated configuration.

FIG. 35 is another cross-sectional view of the articulation joint of the electrosurgical instrument of FIG. 27 in an articulated configuration.

FIG. 36 is a cross-sectional end view of the articulation joint of the electrosurgical instrument of FIG. 27 in an articulated configuration.

FIG. 38 is a perspective view of an electrosurgical instrument comprising a handle, a shaft, and an end effector, wherein the shaft is articulatable relative to the handle.

FIG. 39 illustrates a ball and socket joint configured to permit the shaft of FIG. 38 to articulate relative to the handle.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
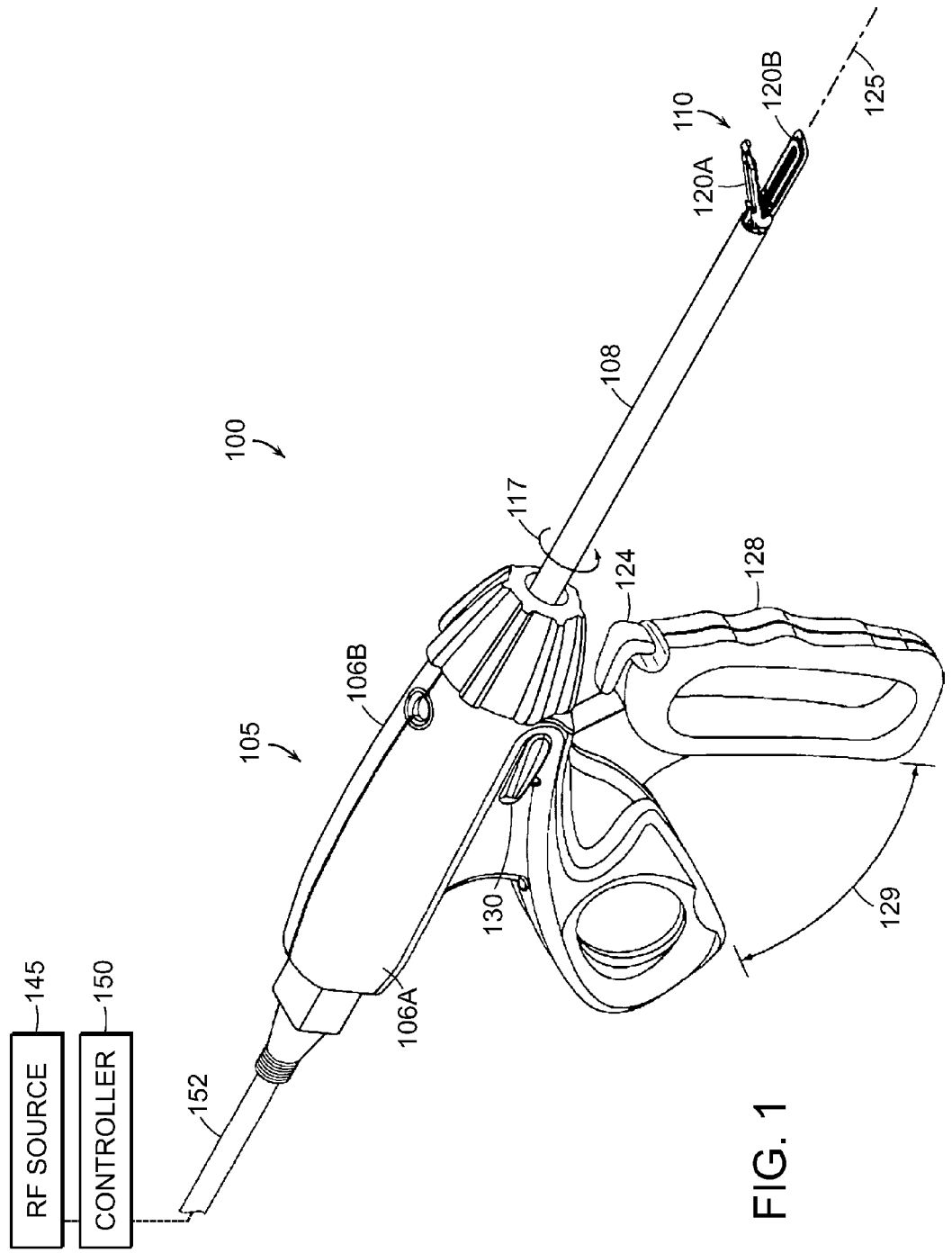
FIG. 1 is a perspective view of an electrosurgical instrument.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

The entire disclosure of the commonly-owned U.S patent application Ser. No. 12/832,345, now U.S. Patent Publication No. 2010/0010616, entitled SURGICAL INSTRUMENT COMPRISING AN ARTICULATABLE END EFFECTOR, filed on even date herewith is hereby incorporated by reference herein.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments disclosed herein provide electrosurgical jaw structures adapted for transecting captured tissue between the jaws and for contemporaneously welding the captured tissue margins with controlled application of RF energy. The jaw structures can comprise a scoring element which can cut or score tissue independently of the tissue capturing and welding functions of the jaw structures. The jaw structures can comprise first and second opposing jaws that carry positive temperature coefficient (PTC) bodies for modulating RF energy delivery to the engaged tissue.

A surgical instrument can be configured to supply energy, such as electrical energy and/or heat energy, for example, to the tissue of a patient. For example, various embodiments disclosed herein can comprise electrosurgical jaw structures adapted for transecting captured tissue positioned between the jaws and for contemporaneously welding margins of the captured tissue with the controlled application of RF energy, for example. Referring now to FIG. 1, an electrosurgical instrument 100 is shown. Electrosurgical instrument 100 can comprise a proximal handle 105, a distal working end or end effector 110, and an introducer or elongate shaft 108 disposed therebetween. End effector 110 may comprise a set of openable and closeable jaws, such as an upper first jaw 120A and a lower second jaw 120B, for example, which can comprise straight and/or curved configurations. First jaw 120A and second jaw 120B may each comprise an elongate slot or channel 142A and 142B (see FIG. 3), respectively, therein disposed within their respective middle portions along axis 152, for example. As described in greater detail below, first jaw 120A and second jaw 120B may be coupled to an electrical source or RF source 145 and a controller 150 through electrical leads in cable 152. Controller 150 may be used to activate electrical source 145.

Figure 2:
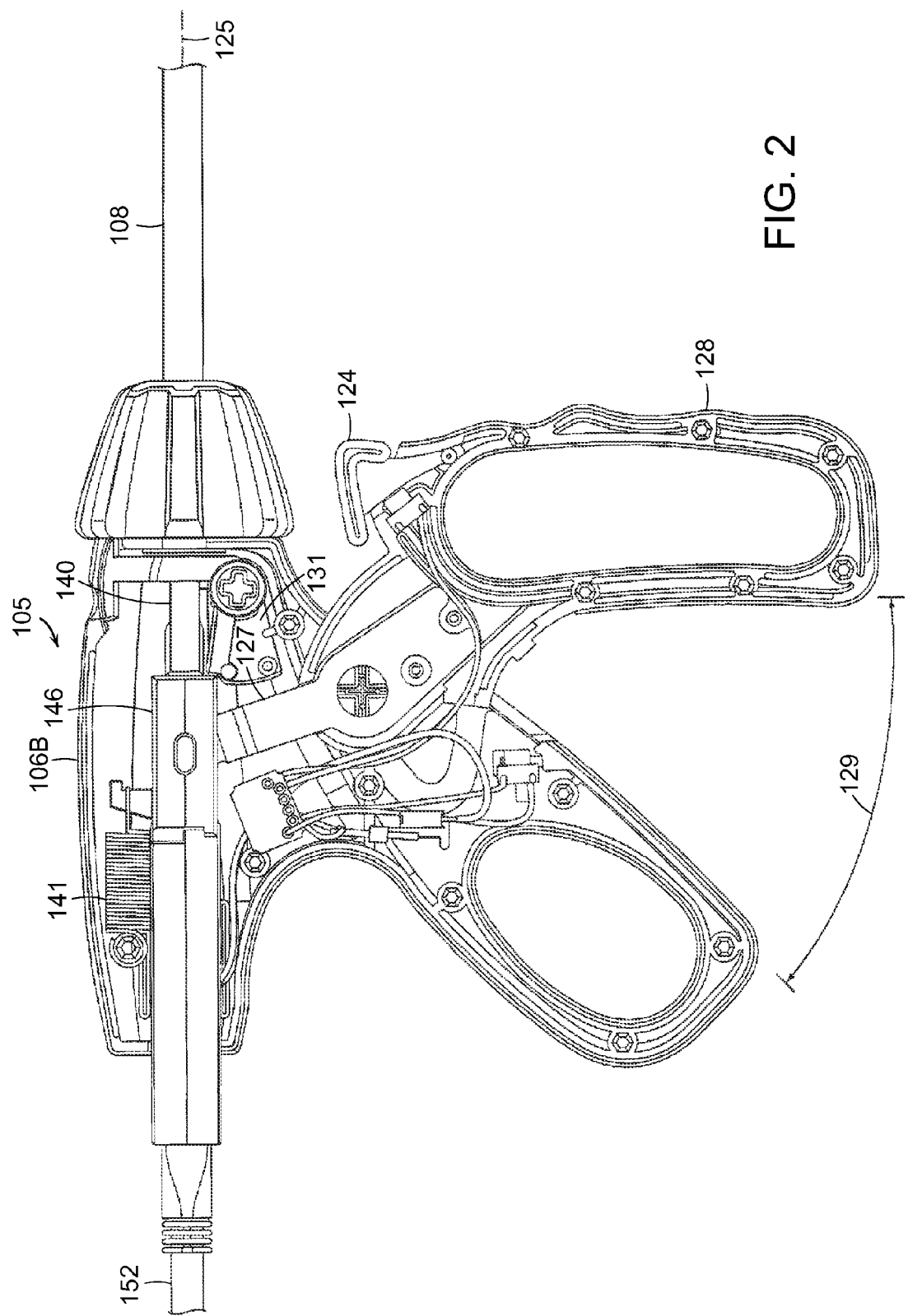
FIG. 2 is a side view of a handle of the surgical instrument of FIG. 1 with a half of a handle body removed to illustrate some of the components therein.

Moving now to FIG. 2, a side view of the handle 105 is shown with a first handle body 106A (see FIG. 1) removed to illustrate some of the components within second handle body 106B. Handle 105 may comprise a lever arm, or trigger, 128 which may be pulled along a path 129. Lever arm 128 may be coupled to a movable cutting member disposed within elongate shaft 108 by a shuttle 146 operably engaged to an extension 127 of lever arm 128. The shuttle 146 may further be connected to a biasing device, such as spring 141, for example, which may also be connected to the second handle body 106B, wherein the spring 141 can be configured to bias the shuttle 146 and thus the cutting member in a proximal direction. When the cutting member is in a proximal position, the jaws 120A and 120B can be urged into an open configuration as seen in FIG. 1 by a jaw spring disposed between a portion of the jaws 120A and 120B, for example. Also, referring to FIGS. 1 and 2, a locking member 131 (see FIG. 2) may be moved by a locking switch 130 (see FIG. 1) between a locked position in which the shuttle 146 can be prevented from moving distally and an unlocked position in which the shuttle 146 may be allowed to freely move in the distal direction toward the elongate shaft 108. The handle 105 can be any type of pistol-grip or other type of handle known in the art that is configured to carry actuator levers, triggers and/or sliders for actuating the first jaw 120A. Elongate shaft 108 may have a cylindrical and/or rectangular cross-section and can comprise a thin-wall tubular sleeve that extends from handle 105. Elongate shaft 108 may include a bore extending therethrough for carrying actuator mechanisms configured to actuate the jaws and/or for carrying electrical leads configured to conduct electrical energy to electrosurgical components of end effector 110.

End effector 110 may be adapted for capturing, welding and transecting tissue. In various embodiments, at least one of first jaw 120A and second jaw 120B may be closed to capture or engage tissue therebetween. First jaw 120A and second jaw 120B may also apply compression to the tissue. Elongate shaft 108, along with first jaw 120A and second jaw 120B, can be rotated a full 360° degrees, as shown by arrow 117, relative to handle 105 through one or more rotary contacts, for example. First jaw 120A and second jaw 120B can remain openable and/or closeable while rotated. Referring now to FIG. 1, end effector 110 may be coupled to electrical source 145 and controller 150. Controller 150 can regulate the electrical energy delivered by electrical source 145 which in turn delivers electrosurgical energy to electrodes within the jaws 120A, 120B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. As described in greater detail below, the electrodes of the jaw members may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

Figure 3:
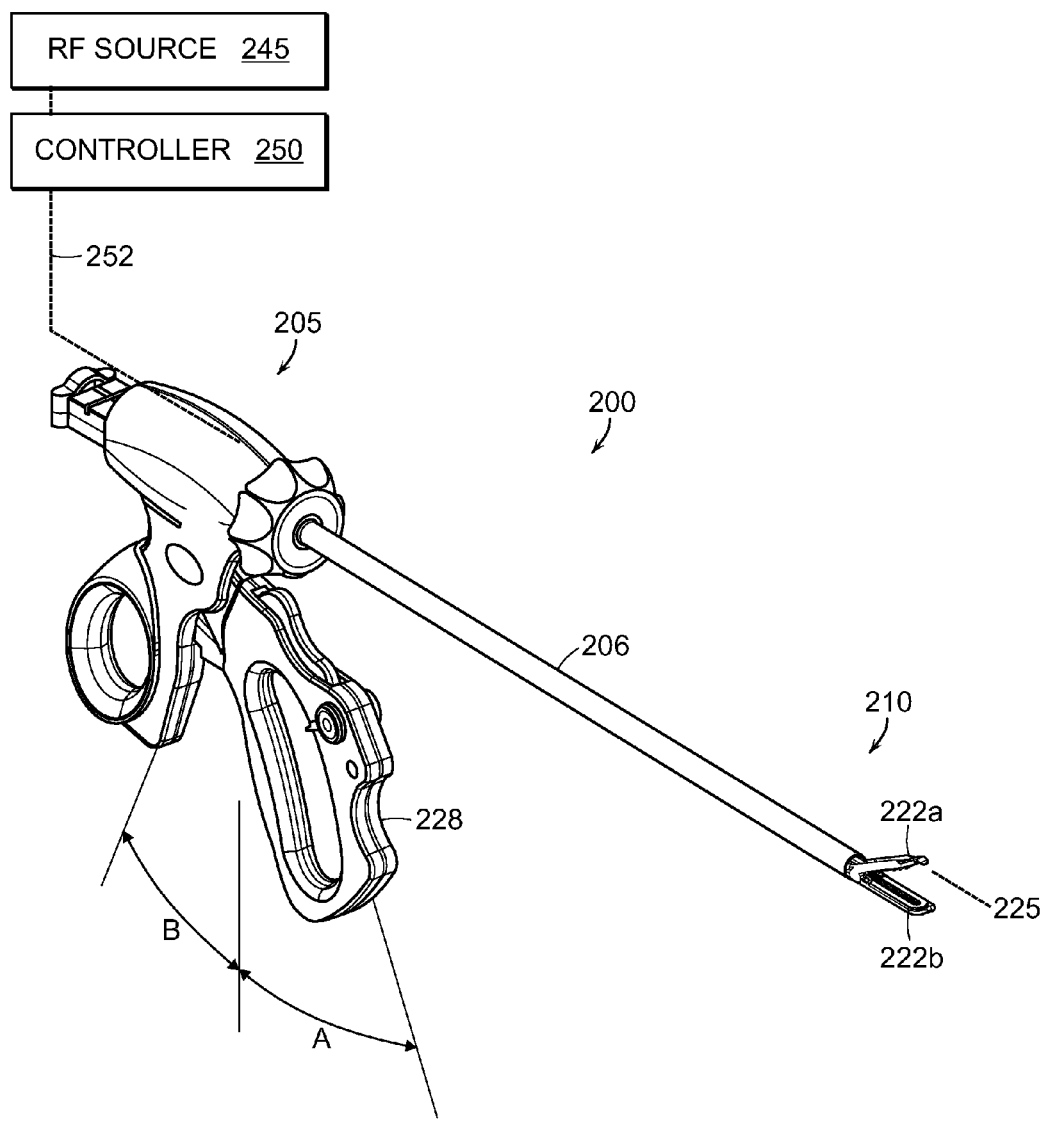
FIG. 3 is a perspective view of an electrosurgical instrument.
Figure 4A:
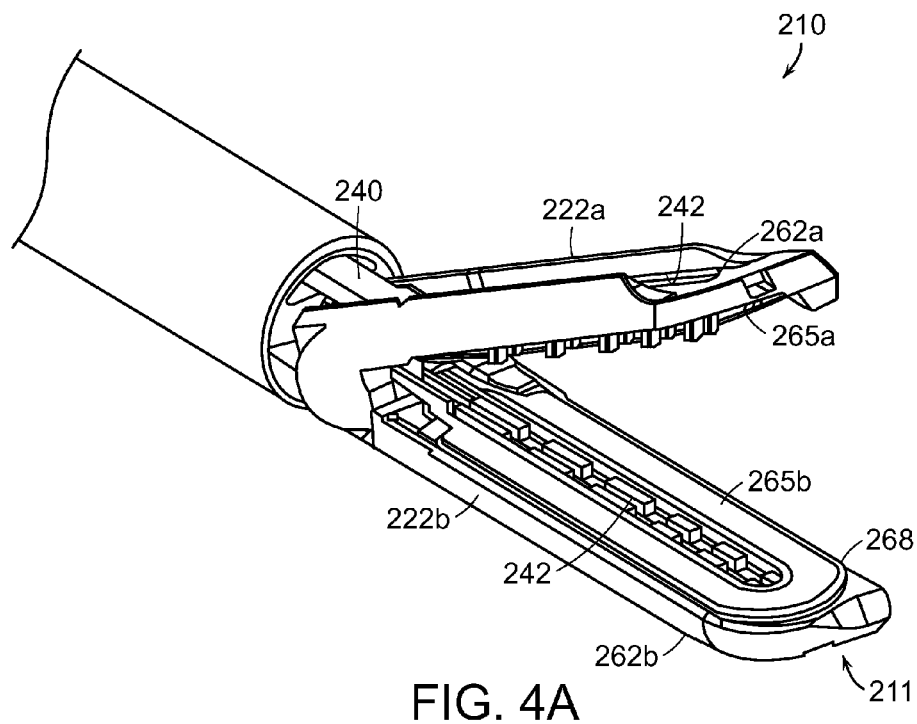
FIG. 4A illustrates an end effector of an electrosurgical instrument in an open configuration.
Figure 4B:
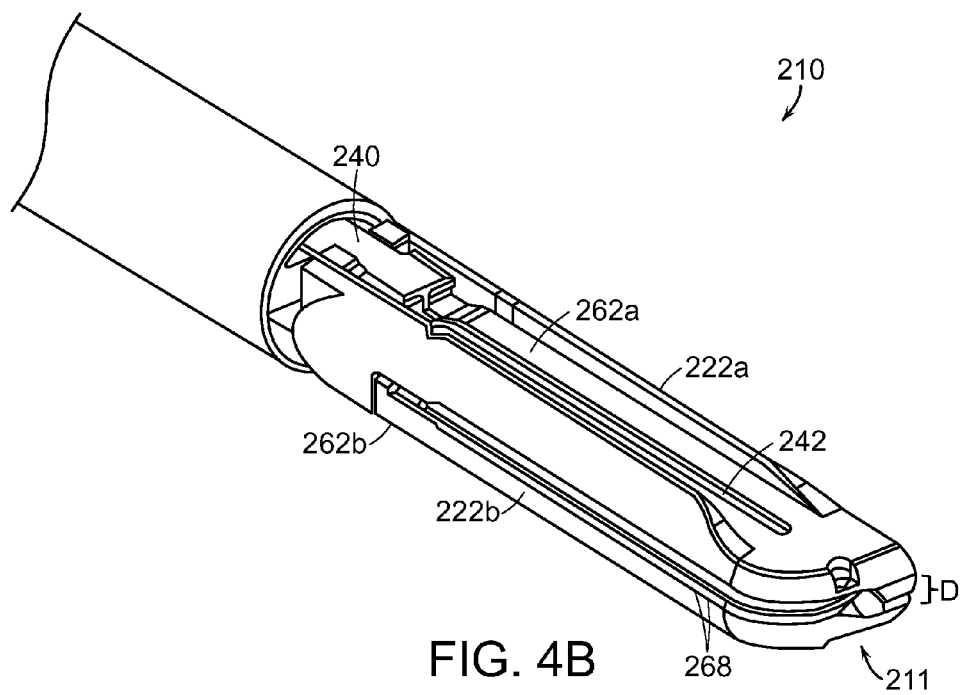
FIG. 4B illustrates the end effector of FIG. 4A in a closed configuration.

FIG. 3 illustrates an electrosurgical instrument 200 comprising a handle end 205, a shaft, or introducer, 206, and an end effector, or working end, 210. Shaft 206 can comprise any suitable cross-section, such as a cylindrical and/or rectangular cross-section, for example, and can comprise a tubular sleeve that extends from handle 205. End effector 210 can extend from shaft 206 and may be adapted for welding and transecting tissue. In various embodiments, end effector 210 can comprise an openable and closeable jaw assembly which can, in various embodiments, comprise straight, curved, and/or any other suitably configured jaws. In various embodiments, the end effector 210 can comprise a first jaw 222a and a second jaw 222b, wherein at least one of the jaws 222a and 222b can move relative to the other. In at least one embodiment, the first jaw 222a can be pivoted about an axis relative to the second jaw 222b in order close onto, capture, and/or engage tissue positioned between the jaws and apply a compression force or pressure thereto. In various embodiments, the handle 205 can comprise a lever arm, or trigger, 228 adapted to actuate a translatable member 240. More particularly, in at least one embodiment, the lever arm 228 can be actuated in order to move member 240 distally toward the distal end 211 of end effector 210 and, when member 240 is advanced distally, member 240 can contact first jaw 222a and move it downwardly toward second jaw 222b, as illustrated in FIG. 4B. In at least one embodiment, the translatable member 240 can comprise a proximal rack portion and the lever arm 228 can comprise a plurality of gear teeth which can be configured to drive the proximal rack portion of translatable member 240 distally. In certain embodiments, rotation of the lever arm 228 in the opposite direction can drive the translatable member 240 proximally.

Figure 4C:
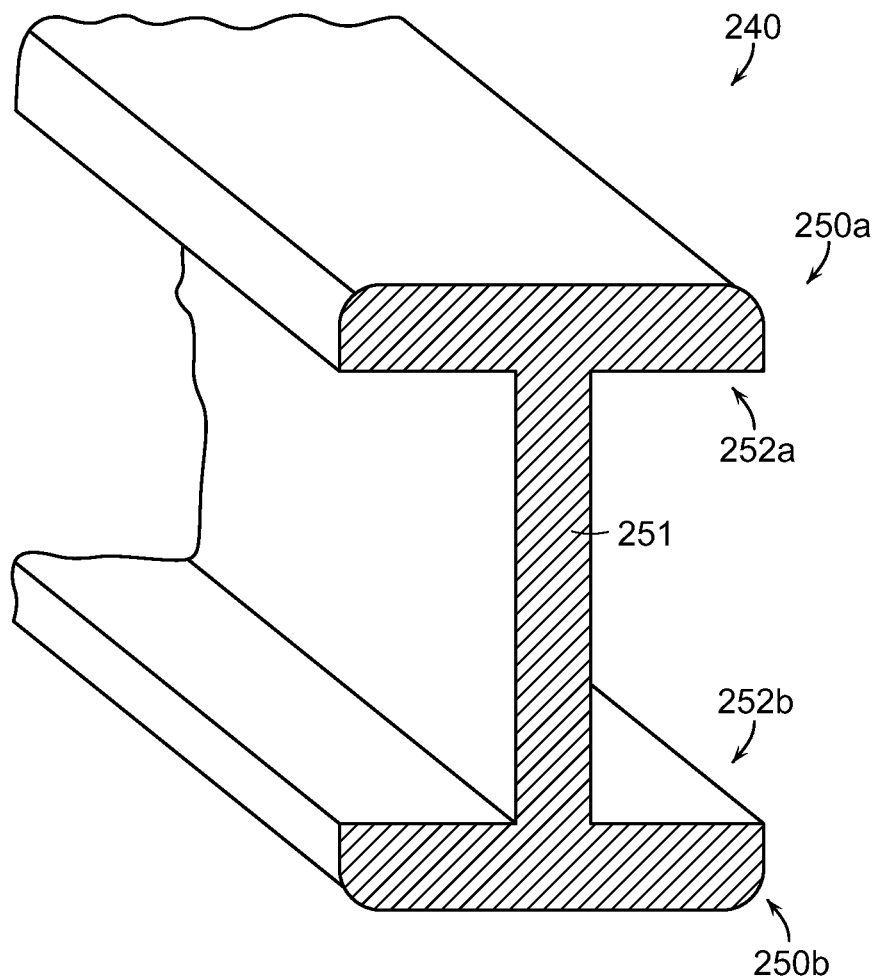
FIG. 4C is a sectional view of a translatable member shaped like an I-beam which is configured to close the end effector of the surgical instrument of FIG. 3.

As described above, the translatable member 240 can be configured to contact first jaw 222a and pivot jaw 222a toward second jaw 222b. In various embodiments, referring now to FIGS. 4A-4C, the distal end of reciprocating member 240 can comprise a flanged "I"-beam configured to slide within a channel 242 in the jaws 222a and 222b. Referring primarily to FIG. 4C, the I-beam portion of member 240 can comprise an upper flange 250a, a lower flange 250b, and a center, or intermediate, portion 251 connecting the flanges 250a and 250b. In at least one embodiment, the flanges 250a and 250b and the center portion 251 can define "c"-shaped channels on the opposite sides of member 240. In any event, in various embodiments, the flanges 250a and 250b can define inner cam surfaces 252a and 252b, respectively, for slidably engaging outward-facing surfaces 262a and 262b of jaws 222a and 222b, respectively. More particularly, the inner cam surface 252a can comprise a suitable profile configured to slidably engage the outer surface 262a of first jaw 222a and, similarly, the inner cam surface 252b can comprise a suitable profile configured to slidably engage the outer surface 262b of second jaw 222b such that, as translatable member 240 is advanced distally, the cam surfaces 252a and 252b can co-operate to cam first jaw member 222a toward second jaw member 222b and configure the end effector 240 in a closed configuration. As seen in FIG. 4B, jaws 222a and 222b can define a gap, or dimension, D between the first and second electrodes 265a and 265b of jaws 222a and 222b, respectively, when they are positioned in a closed configuration. In various embodiments, dimension D can equal a distance between approximately 0.0005" to approximately 0.005", for example, and, in at least one embodiment, between approximately 0.001" and approximately 0.002", for example.

As discussed above, the translatable member 240 can be at least partially advanced in order to move the first jaw 222a toward the second jaw 222b. Thereafter, the movable member 240 can be advanced further distally in order to transect the tissue positioned between the first jaw 222a and the second jaw 222b. In certain embodiments, the distal, or leading, end of the I-beam portion of 240 can comprise a sharp, or knife, edge which can be configured to incise the tissue. Before, during, and/or after the member 240 is advanced through the tissue, electrical current can be supplied to the electrodes in the first and second jaw members in order to weld the tissue, as described in greater detail further below. In various circumstances, the operation of the trigger 228 can advance the knife edge of the cutting member 240 to the very distal end of slot or channel 242. After the cutting member 240 has been sufficiently advanced, the trigger 288 can be released and moved into its original, or unactuated, position in order to retract the cutting member 240 and allow first jaw 222a to move into is open position again. In at least one such embodiment, the surgical instrument can comprise a jaw spring configured to bias the first jaw 222a into its open position and, in addition, a trigger spring configured to bias the trigger 228 into its unactuated position.

In various embodiments, further to the above, the surgical instrument can comprise a first conductor, such as an insulated wire, for example, which can be operably coupled with the first electrode 265a in first jaw member 222a and, in addition, a second conductor, such as an insulated wire, for example, which can be operably coupled with the second electrode 265b in second jaw member 222b. In at least one embodiment, referring again to FIG. 3, the first and second conductors can extend through shaft 206 between an electrical connector in handle 205 and the electrodes 265a and 265b in the end effector 210. In use, the first and second conductors can be operably coupled to electrical source 245 and controller 250 by electrical leads in cable 252 in order for the electrodes 265a and 265b to function as paired bi-polar electrodes with a positive polarity (+) and a negative polarity (−). More particularly, in at least one embodiment, one of the first and second electrodes 265a and 265b can be operably coupled with a positive (+) voltage terminal of electrical source 245 and the other of the first and second electrodes 265a and 265b can be electrically coupled with the negative voltage (−) terminal of electrical source 245. Owing to the opposite polarities of electrodes 265a and 265b, current can flow through the tissue positioned between the electrodes 265a and 265b and heat the tissue to a desired temperature. In certain embodiments, the cutting member 240 can act as an electrode when it is electrically coupled to a positive terminal or negative terminal of the source 245, and/or any suitable ground.

Figure 5:
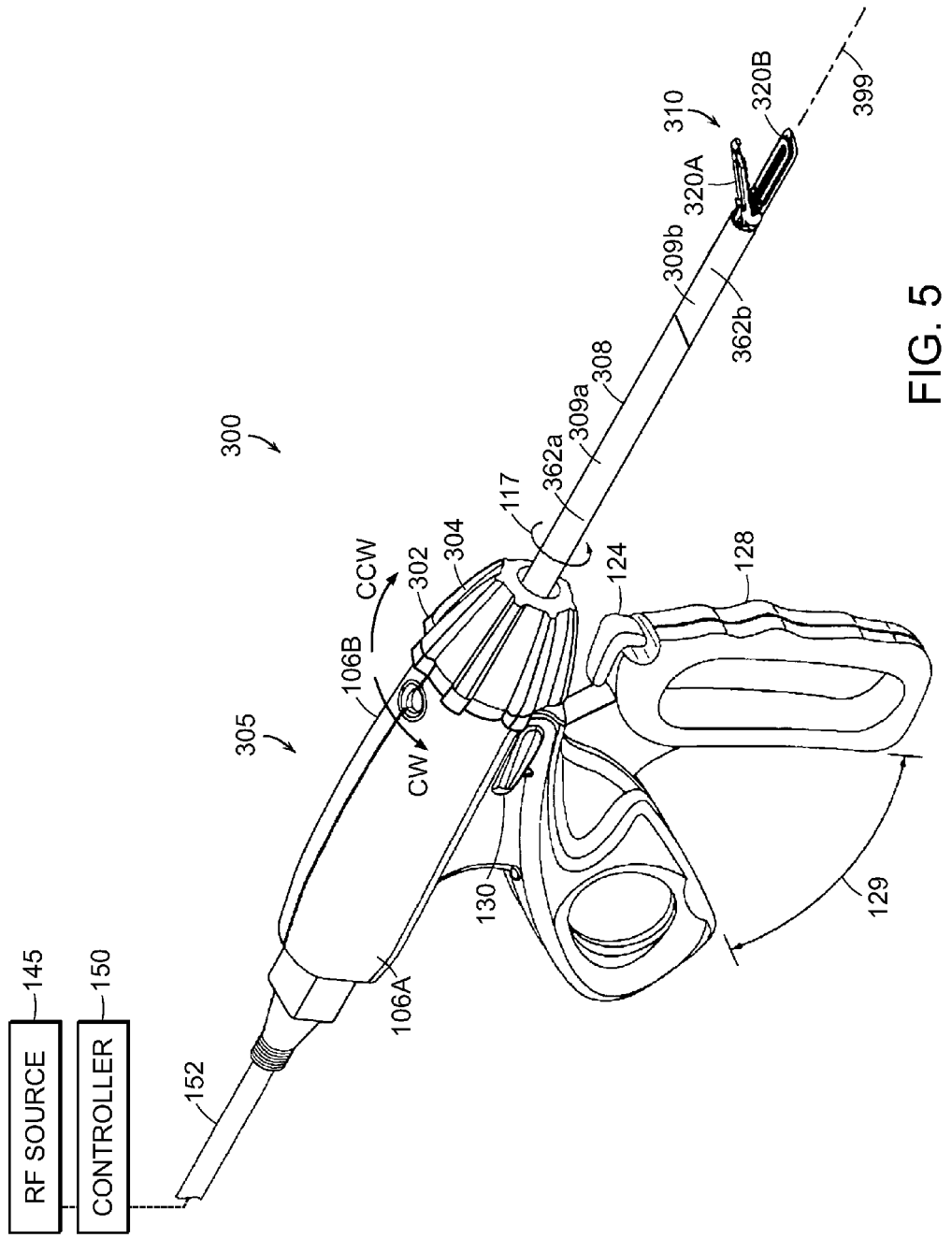
FIG. 5 is a perspective view of an electrosurgical instrument.

In the embodiments described above, an electrosurgical instrument can comprise a shaft and an end effector, wherein the end effector may not articulate relative to the shaft. In at least one embodiment, the shaft can comprise a rigid spine and/or rigid outer housing which can be mounted to the end effector and a handle of the electrosurgical instrument. In at least one such embodiment, a jaw member of the end effector can be rigidly mounted to the spine and/or outer housing of the shaft. In certain embodiments, referring now to FIGS. 5-7, an electrosurgical instrument, such as instrument 300, for example, can comprise an end effector 310 which can be articulated relative to a shaft 308. Similar to the above, the end effector 310 can comprise a first jaw 320A which is pivotably connected to a second jaw 320B, wherein the second jaw 320B can be mounted to at least a portion of shaft 308. In at least one such embodiment, referring to FIG. 5, the shaft 308 can comprise, one, a proximal portion 309A mounted to a handle 305 of the surgical instrument 300 and, two, a distal portion 309B mounted to second jaw 320B of the end effector 310. In various embodiments, the proximal portion 309A of shaft 308 can comprise a proximal outer housing 362A and the distal portion 309B of shaft 308 can comprise a distal outer housing 362B. The shaft 308 can further comprise a spine 364 extending through apertures defined within the outer housings 362A and 362B wherein, in at least one such embodiment, the spine 364 can be mounted to the distal outer housing 362B such that longitudinal movement, or displacement, of the distal portion 309B relative to the proximal portion 309A can be prevented, or at least substantially inhibited. As discussed in greater detail below, adjacent portions of the outer housings 362A and 362B can comprise an articulation joint 360.

Figure 6:
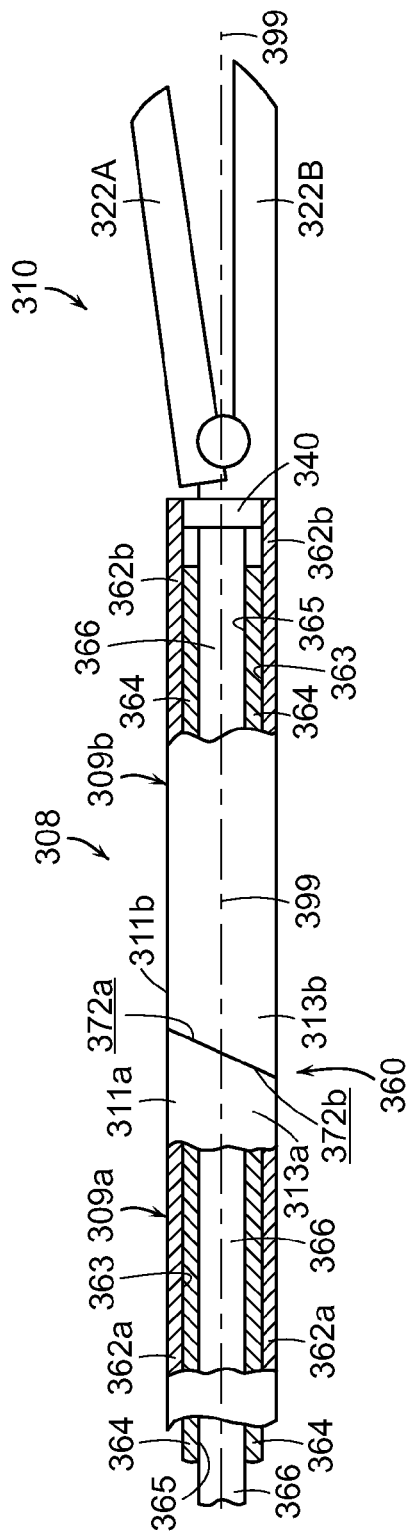
FIG. 6 is partial cross-sectional view of a shaft and an end effector of the electrosurgical instrument of FIG. 5.

In addition to the above, the spine 364 can comprise an actuator configured to rotate distal outer housing 362b and end effector 310 relative to proximal outer housing 362a. In various embodiments, the spine 364 can be fixedly mounted to distal outer housing 362b such that, when the spine 364 is rotated about longitudinal axis 399, the distal outer housing 362b is also rotated about axis 399. When the distal outer housing 362b is rotated, referring now to FIG. 7, the distal outer housing 362b can be cammed or rotated laterally relative to axis 399 as illustrated in FIG. 6. In at least one such embodiment, the proximal outer housing 362a can comprise a cam 372a against which the distal outer housing 362b can be positioned, or positioned closely adjacent to, such that, when the distal outer housing 362b is rotated, the cam 372a can cause the distal outer housing 362b to pivot to the side. In various embodiments, the cam 372a can comprise an angled surface and the distal outer housing 362b can comprise an opposing angled surface, or cam follower, 372b, wherein, in at least one embodiment, the angled surface 372b can be parallel, or at least substantially parallel, to the angled surface of cam 372a. As a result of the above, referring again to FIGS. 6 and 7, the distal shaft portion 309b and end effector 310 can be rotated about a longitudinal axis and articulated about a different axis simultaneously. More particularly, as distal shaft portion 309b and end effector 310 are rotated about longitudinal axis 399, as described above, the distal shaft portion 309b and end effector 310 can be pivoted about an axis 398 which is perpendicular, or at least substantially perpendicular, to longitudinal axis 399. In the embodiment depicted in FIGS. 6 and 7, the distal shaft portion 309b can be rotated such that a first lateral side 311b of distal shaft portion 309b is positioned adjacent to a first lateral side 311a of the proximal shaft portion 309a when the distal shaft portion 309b is in an unarticulated position and, after the distal shaft portion 309b has been articulated, the first lateral side 311b of distal shaft portion 309b can be positioned adjacent to a second lateral side 313a of proximal shaft portion 309a and, similarly, a second lateral side 313b of distal shaft portion 309b can be positioned adjacent to the first lateral side 311a of proximal shaft portion 309a.

Figure 7:
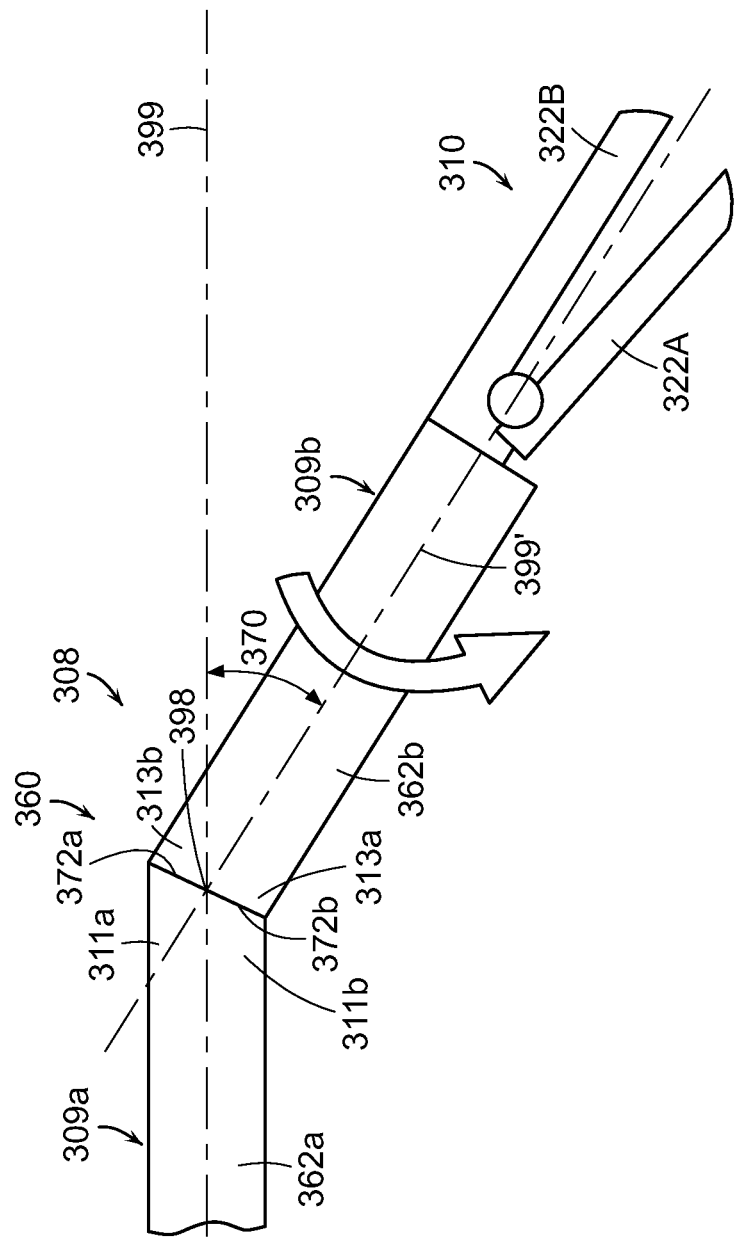
FIG. 7 illustrates the end effector of FIG. 6 in a rotated and articulated configuration.

In certain embodiments, the angled surface of cam 372a can be oriented at an approximately 22.5 degree angle, or an approximately 45 degree angle, for example, with respect to longitudinal axis 399. In embodiments where the angled surface of cam 372a is oriented at an approximately 22.5 degree angle with respect to axis 399, the angled surface of cam follower 372b can also be oriented at an approximately 22.5 degree angle with respect to axis 399, for example. In embodiments where the angled surface of cam 372a is oriented at an approximately 45 degree angle with respect to axis 399, the angled surface of cam follower 372b can be oriented at an approximately 45 degree angle with respect to axis 399, for example. In various embodiments, the spine 364 can be rotated for approximately 20 degrees about longitudinal axis 399 and, owing to the configuration of the co-operating cam and cam follower of the outer housings 362a and 362b, the distal portion 309B and end effector 310 can be rotated approximately 10 degrees, for example. Similarly, the spine 364 can be rotated approximately 90 degrees to produce an approximately 45 degree articulation of distal portion 309B and end effector 310, for example. Likewise, the spine 364 can be rotated approximately 180 degrees to produce an approximately 90 degree articulation of distal portion 309B and end effector 310, for example. In at least one embodiment, the degree in which spine 364 is rotated about axis 399 can result in a change in the articulation angle of distal outer housing 362b which is less than that amount. Such an articulation angle is depicted in FIG. 7 as angle 370 which is defined between the unarticulated longitudinal axis 399 of shaft 308 and the articulated longitudinal axis 399' of distal portion 309B. The ratio between the rotation of spine 364 and the articulation of distal outer housing 362b can depend on the angle of cam surface 372a and/or the angle of cam follower surface 372b. Various ratios are contemplated such as about 1.5:1, about 2:1, and/or about 4:1, for example.

Figure 8:
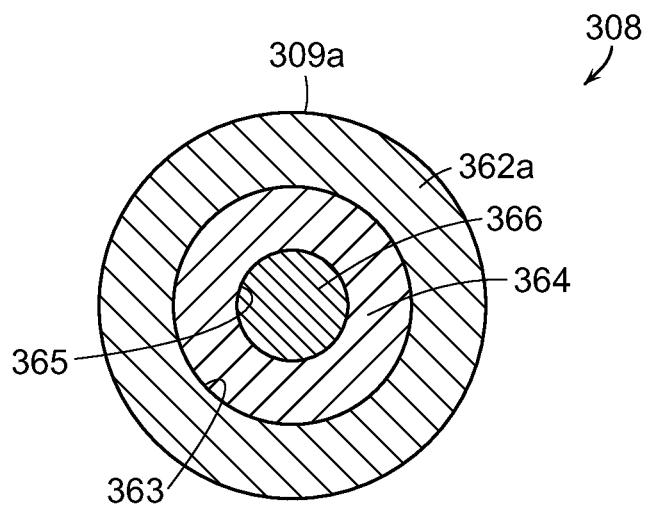
FIG. 8 is a cross-sectional view of the shaft of FIG. 6.
Figure 11:
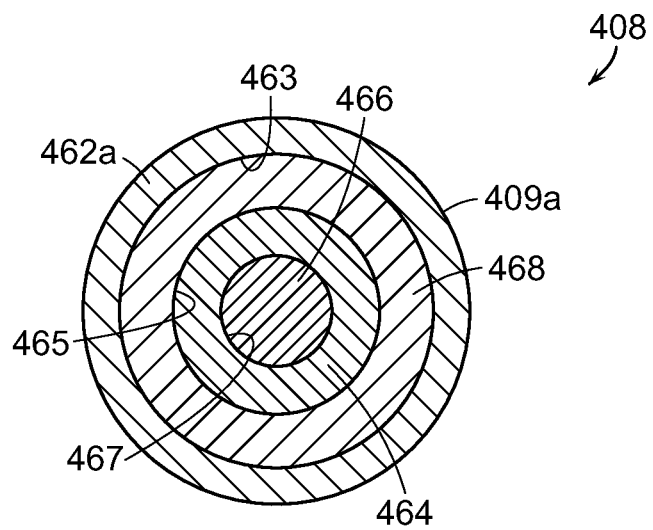
FIG. 11 is a cross-sectional view of the shaft of FIG. 9.

In various embodiments, further to the above, the spine 364 can be sufficiently stiff so as to transmit a rotational torque to the distal shaft portion 309b but sufficiently flexible in order to bend within articulation joint 360 and accommodate the articulation of distal shaft portion 309b. Referring now to FIG. 8, the spine 364 can be configured to rotate within a cavity 363 defined within the outer housing portion 362a such that the spine 364 can rotate relative to proximal outer housing 362a. In various embodiments, the spine 364 can be closely received within the cavity 363 such that the outer perimeter of the spine 364 is positioned adjacent to the inner sidewalls of the cavity 363. In at least one embodiment, referring now to FIG. 5, the surgical instrument 300 can further comprise an articulation actuator 302 operably engaged with the spine 364 such that, when the actuator 302 is rotated about axis 399, the spine 364 is also rotated about axis 399. In at least one such embodiment, the spine 364 can be rotated in a clockwise direction, indicated by arrow CW, when actuator 302 is rotated in direction CW and, correspondingly, the spine 364 can be rotated in a counter-clockwise direction, indicated by arrow CCW, when actuator 302 is rotated in direction CCW, for example. In at least one embodiment, the actuator 302 can comprise one or more projections and/or one or more grooves which can be configured to allow a surgeon to easily grip and manipulate the actuator 302. In certain embodiments, the handle 305 can further comprise a locking mechanism which can be configured to releasably hold actuator 302 in position. In at least one such embodiment, although not illustrated, the handle 305 can comprise a biasing member, such as a spring, for example, which can be configured to bias actuator 302 against a locking plate configured to hold actuator 302 in position and prevent end effector 310 from being articulated. In use, the actuator 302 can be pulled proximally against the biasing force of the biasing member, for example, and away from the locking plate in order to disengage actuator 302 from the locking plate. Thereafter, the actuator 302 can be rotated about axis 399 in order to articulate end effector 310. Once end effector 310 has been suitably articulated, the actuator 302 can be released thereby allowing the biasing spring to position the actuator 302 into engagement with the locking plate once again.

In various embodiments, further to the above, the shaft 308 of surgical instrument 300 can further comprise a shaft actuator 304 which can be mounted to proximal outer housing portion 362a. The shaft actuator 304 can be mounted to shaft 308 such that the rotation of shaft actuator 304 can rotate shaft 308 and end effector 310 about longitudinal axis 399. In at least one embodiment, the shaft actuator 304 can be utilized to rotate the shaft 308 and end effector 310 without rotating the spine 364 relative to proximal shaft portion 309a and, in addition, without articulating the end effector 310. In at least one such embodiment, the articulation actuator 302 can be releasably engageable with the shaft actuator 304 wherein, when the articulation actuator 302 is engaged with the shaft actuator 304, the actuator 302 can be rotated with the actuator 304 without articulating the end effector 310 and wherein, when the actuator 302 is disengaged from the shaft actuator 304, the rotation of one of actuator 302 or actuator 304 relative to the other can articulate the end effector 310 in either the CW or CCW directions, depending on the direction of relative rotation between the actuators 302 and 304. In certain embodiments, the shaft actuator 304 can comprise the locking plate against which the articulation actuator 302 can be biased in order to releasably lock the actuator 302, and the articulation angle of end effector 310, into position. In various embodiments, although not illustrated, the handle 305 can further comprise a second locking plate, for example, against which the shaft actuator 304 can be biased in order to releasably hold shaft actuator 304 in position. In at least one such embodiment, similar to the above, the handle 305 can comprise a second biasing member configured to bias the shaft actuator 304 against the second locking plate in order to hold it in position. In various embodiments, as a result of the above, the articulation actuator 302 and the shaft actuator 304 can be operated independently of one another and/or concurrently with one another.

Figure 13:
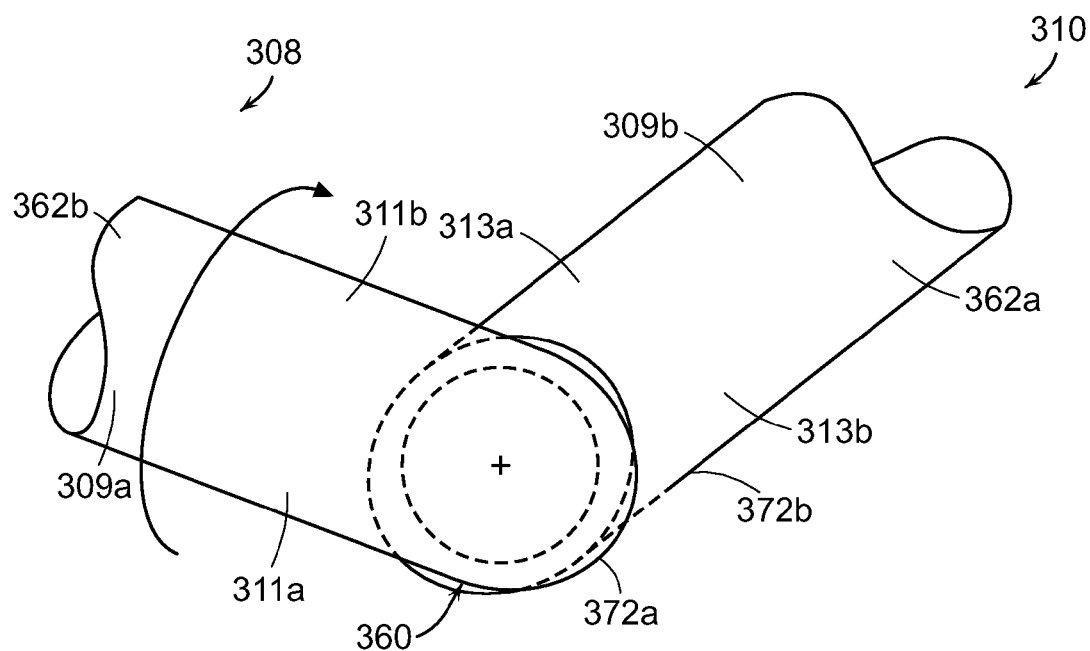
FIG. 13 is a perspective view of an articulation joint about which an end effector can be rotated.

Referring now to FIG. 13, the distal shaft portion 309b of shaft 308 is depicted as being articulated relative to the proximal shaft portion 309a. During such articulation, the angled surface 372b of distal shaft portion 309b can be configured to contact and slide across the face of the angled surface 372a of proximal shaft portion 309a. In various embodiments, the outer housings 362a and 362b of shaft portions 309a and 309b, respectively, can be circular, or at least substantially circular, in cross-section and, owing to the angled surfaces 372a and 372b, the end faces formed by the angled surfaces 372a and 372b can be oval, or at least substantially oval, in shape. Although these opposing end faces may be oval, in various embodiments, the distal shaft portion 309b can be rotated about a longitudinal axis such that the distal shaft portion 309b is rotated in a circular manner relative to proximal shaft portion 309a. Such a circular relationship is depicted in FIG. 13. In at least one such embodiment, the spine 364 and/or the outer housing 362b of distal shaft portion 309b can be rotated concentrically about the longitudinal axis extending therethrough. In various embodiments, the surgical instrument 300 can further comprise a biasing or tensioning device, such as a spring, for example, which can be configured to apply a biasing force to the spine 364 such that the cam follower surface 372b of distal shaft portion 309b is positioned against, and remains in contact with, the cam surface 372a of proximal shaft portion 309a.

In various embodiments, the surgical instrument 300 can further comprise a drive member, such as drive member 366, for example, which can be operably coupled with a cutting member 340 positioned within the end effector 310. The drive member 366 can be operably coupled with a trigger, such as trigger 128 (FIG. 1), for example, of the surgical instrument handle and can extend through a cavity 365 (FIG. 6) defined within the spine 364 of the shaft 308. In various embodiments, the outer housings 362a, 362b, the cavity 363 defined within the outer housings 362a, 362b, the spine 364, the cavity 365 extending through spine 364, and the drive member 366 can be concentrically, or at least substantially concentrically, positioned along a common axis. In at least one such embodiment, the drive member 366 can be closely received within the cavity 365 such that the outer perimeter of drive member 366 is positioned adjacent to the inner sidewalls of cavity 365. In various embodiments, the outer housings 362a, 362b and spine 364 can each comprise a tubular or cylindrical configuration and the drive shaft 366 can comprise a cylindrical rod, for example. In any event, the trigger 128 can be actuated in order to move the drive member 366 between a proximal position and a distal position in order to advance the cutting member 340, and/or an I-beam member, distally within the end effector 310.

Figure 9:
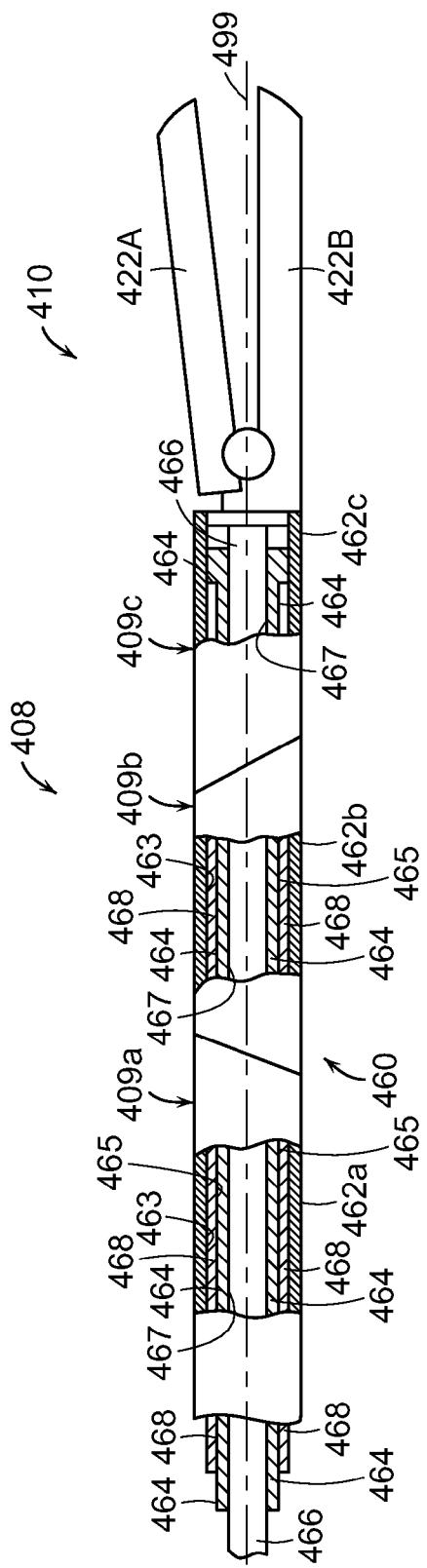
FIG. 9 is a partial cross-sectional view of a shaft and an end effector of an electrosurgical instrument in accordance with an alternative embodiment.
Figure 10:
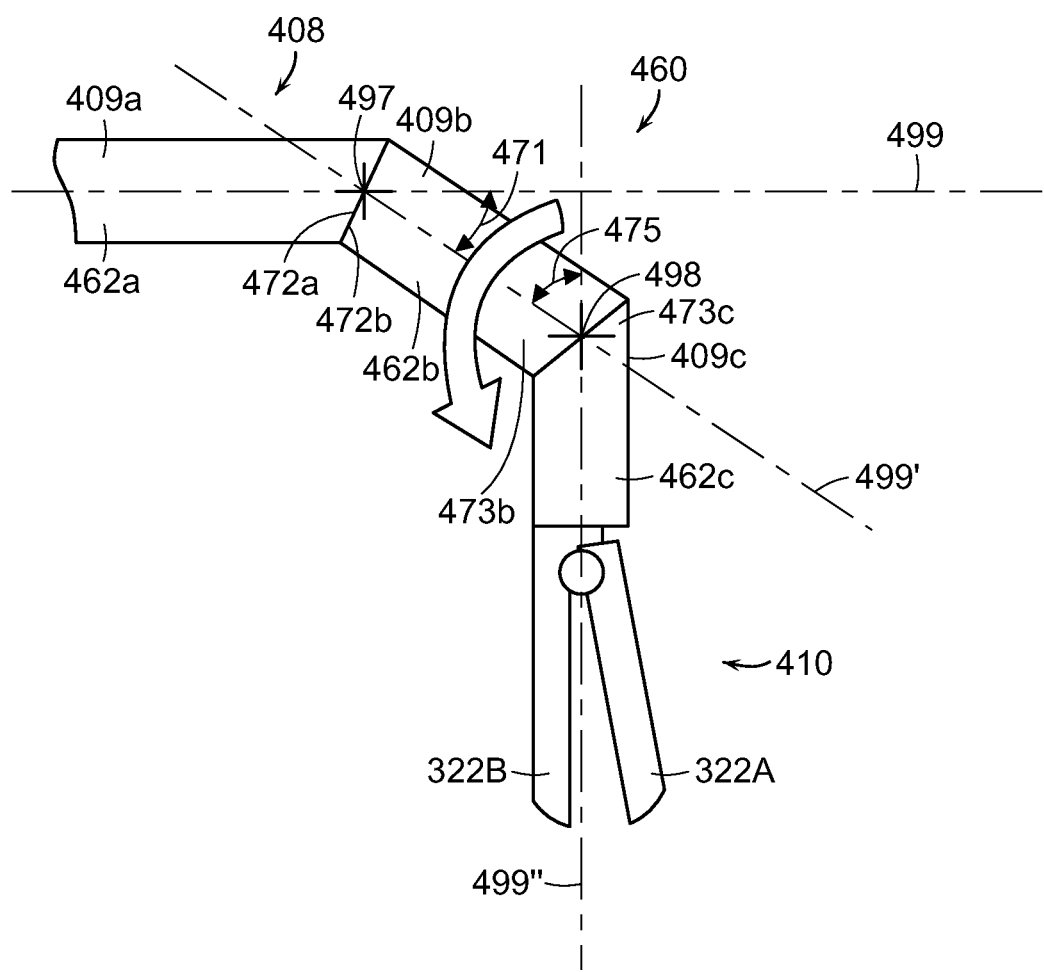
FIG. 10 illustrates the end effector of FIG. 9 in an articulated configuration.
Figure 12:
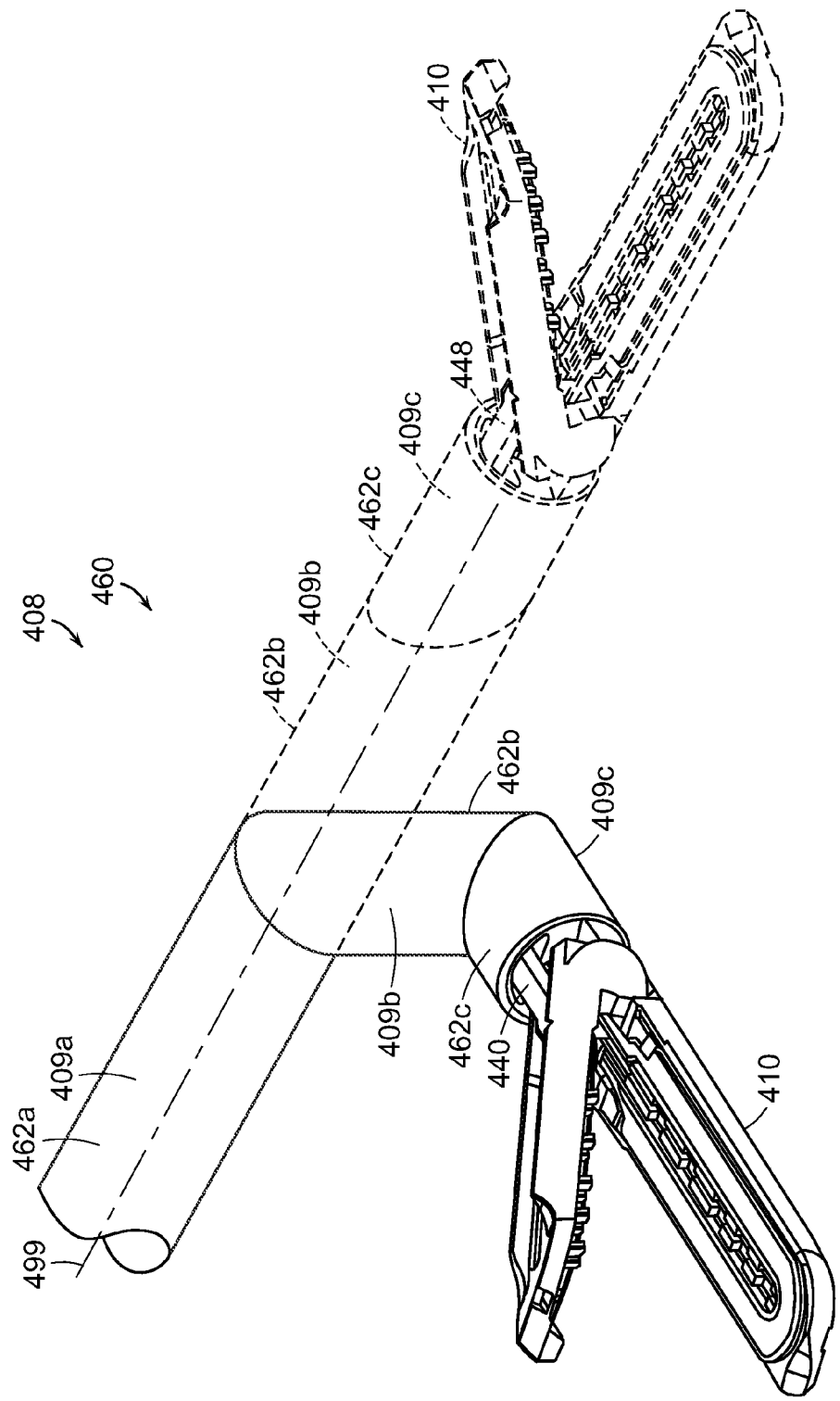
FIG. 12 is a perspective view illustrating the end effector of FIG. 9 in an unarticulated configuration, illustrated with phantom lines, and an articulated position, illustrated with solid lines.

In various embodiments, referring now to FIGS. 9, 10, and 12, a surgical instrument, such as surgical instrument 400, for example, can comprise a shaft 408 comprising an articulation joint 460. Similar to the above, the shaft 408 can comprise a proximal shaft portion 409a mounted to a handle of the surgical instrument 400 and a distal shaft portion 409c mounted to an end effector 410. The shaft 408 can further comprise an intermediate shaft portion 409b positioned between the proximal shaft portion 409a and the distal shaft portion 409c. As described in greater detail below, and referring to FIG. 10, the intermediate shaft portion 409b can be configured to permit the articulation joint 460 to articulate about two axes of rotation, i.e., first axis 497 and second axis 498, for example.

In various embodiments, referring primarily to FIG. 9, the shaft 408 can include an outer housing comprised of a proximal outer housing portion 462*a*, an intermediate housing portion 462*b*, and a distal outer housing portion 462*c*. The shaft 408 can further comprise an articulation actuator 468 positioned within a cavity 463 extending through the outer housing portions 462*a* and 462*b*, a spine 464 positioned within a cavity 465 extending through the articulation actuator 468, and a drive member 466 positioned within a cavity 467 extending through the spine 464. The spine 464 can extend through proximal shaft portion 409*a* and intermediate shaft portion 409*b* and can be rigidly mounted to, one, at least one of the handle of the surgical instrument and the proximal outer housing 462*a* and, two, at least one of the end effector 410 and distal outer housing 462*c*. In various embodiments, the spine 464 can be sufficiently stiff so as to prevent, or at least substantially inhibit, the distal shaft portion 409*c* and end effector 410 from rotating relative to the proximal shaft portion 409*a* about longitudinal axis 499 and/or translating distally relative to the intermediate shaft portion 409*b*. In at least one such embodiment, the articulation actuator 468 can be mounted to intermediate outer housing 462*b* such that, when the articulation actuator 468 is rotated about longitudinal axis 499, the intermediate shaft portion 409*b* can be rotated relative to both the proximal shaft portion 409*a* and the distal shaft portion 409*c*. More particularly, the intermediate outer housing 462*b* can be rotated relative to both the proximal outer housing 462*a* and the distal outer housing 462*c*. Owing to such relative rotation, the intermediate shaft portion 409*b* can articulate relative to the proximal shaft portion 409*a* and, in addition, the distal shaft portion 409*c* can articulate relative to the intermediate shaft portion 409*b*.

In various embodiments, referring again to FIGS. 9 and 10, the proximal outer housing 462*a* can comprise a first cam surface 472*a* and the intermediate outer housing 462*b* can comprise a first cam follower surface 472*b* which can be configured to contact the first cam surface 472*a* when the intermediate shaft portion 409*b* is rotated relative to the proximal shaft portion 409*a*. Similar to the above, the rotation of first cam follower surface 472*b* relative to first cam surface 472*a* can cause the intermediate shaft portion 409*b* to pivot or rotate relative to proximal shaft portion 409*a* about first axis 497. In at least one such embodiment, the first cam surface 472*a* can comprise an angled surface which extends transversely to longitudinal axis 499 and, similarly, the first cam follower surface 472*b* can comprise an angled surface which also extends transversely to longitudinal axis 499. In the illustrated embodiment of FIG. 9, the surfaces 472*a*, 472*b* can be parallel, or at least substantially parallel, to one another and can lie within planes that extend through the longitudinal axis 499 at an approximately 22.5 degree angle, for example. As the intermediate shaft portion 409*b* is rotated relative to the proximal shaft portion 409*a*, referring now to FIG. 10, the intermediate shaft portion 409*b* can be positioned along an articulated longitudinal axis 499' which intersects and makes an angle with the unarticulated longitudinal axis 499. In various circumstances, an approximately 180 degree rotation of intermediate shaft portion 409*b* about its longitudinal axis can result in an approximately 45 degree articulation of the intermediate shaft portion 409*b* relative to the proximal shaft portion 409*a*, for example. In various other circumstances, although not illustrated, an approximately 90 degree rotation of shaft portion 409*b* can result in an approximately 22.5 degree articulation of intermediate shaft portion 409*b* relative to proximal shaft portion 409*a*, for example.

Referring again to FIG. 10, the rotation of intermediate outer housing 462*b* of intermediate shaft portion 409*b* about its longitudinal axis can also cause distal shaft portion 409*c* to articulate relative to intermediate shaft portion 409*b*. Such relative articulation between shaft portions 409*b* and 409*c* can be possible owing to the spine 464 which can prevent the distal shaft portion 409*c* from rotating relative to proximal shaft portion 409*a*. Stated another way, the rotation of articulation actuator 464 may not be transmitted to distal shaft portion 409*c* wherein, as a result, the intermediate outer housing 462*b* can rotate relative to both the proximal outer housing 462*a* and the distal outer housing 462*c*. Similar to the above, the distal outer housing 462*c* can comprise a second cam surface 473*c* and the intermediate outer housing 462*b* can comprise a second cam follower surface 473*b* which can which can be configured to contact the second cam surface 473*c* when the intermediate outer housing 426*b* is rotated relative to the distal outer housing 462*c*. Similar to the above, the rotation of second cam follower surface 473*b* relative to second cam surface 473*c* can cause the distal shaft portion 409*c* to pivot or rotate relative to the intermediate shaft portion 409*b* about second axis 498. In at least one such embodiment, referring again to FIG. 9, the second cam surface 473*c* can comprise an angled surface which extends transversely to longitudinal axis 499 and, similarly, the second cam follower surface 473*b* can comprise an angled surface which also extends transversely to longitudinal axis 499. In the illustrated embodiment of FIG. 9, the surfaces 473*b*, 473*c* can be parallel, or at least substantially parallel, to one another and can lie within planes that extend through the longitudinal axis 499 at an approximately 22.5 degree angle, for example. As the intermediate shaft portion 409*b* is rotated relative to the distal shaft portion 409*c*, referring now to FIG. 10, the distal shaft portion 409*c* can be positioned along an articulated longitudinal axis 499" which intersects and makes an angle with the articulated longitudinal axis 499' of intermediate shaft portion 409*b*. In various circumstances, an approximately 180 degree rotation of intermediate shaft portion 409*b* about its longitudinal axis can result in an approximately 45 degree articulation of distal shaft portion 409*c* relative to the intermediate shaft portion 409*b*, for example. In various other circumstances, although not illustrated, an approximately 90 degree rotation of shaft portion 409*b* can result in an approximately 22.5 degree articulation of distal shaft portion 409*c* relative to intermediate shaft portion 409*b*, for example.

In various embodiments, the articulation actuator 468 can be operably coupled with an actuator on the handle of the surgical instrument, such as actuator 302 (FIG. 5), for example, wherein, similar to the above, the actuator 302 can be configured to rotate the articulation actuator 468 in at least one of a clockwise direction (CW) and a counter-clockwise direction (CCW) about longitudinal axis 499. As discussed above, referring again to FIG. 9, the articulation actuator 468 can be mounted to the intermediate outer housing portion 462*b* such that, when actuator 468 is rotated, the outer housing portion 462*b* can be rotated with actuator 468. In various embodiments, the actuator 468 can be tubular, or at least substantially tubular, and can be closely received by the sidewalls of cavity 463 within proximal outer housing 462*a*. The outer perimeter of actuator 468 can be circular, or at least substantially circular, and the inner sidewalls of cavity 463 can also be circular, or at least substantially circular, such that actuator 468 can rotate relative to the proximal outer housing 462*a*. As also described above, the spine 464 can extend through the cavity 465 in actuator 468 and can be mounted to the distal outer housing 462*c*. Similar to actuator 468, spine 464 can be tubular, or at least substantially tubular, and can be closely received by the sidewalls of cavity 465. The outer perimeter of spine 464 can be circular, or at least substantially circular, and the inner sidewalls of cavity 465 can also be circular, or at least substantially circular, such that the actuator 468 can rotate relative to the spine 464.

Similar to the above, the orientation of the angled surfaces of cams 472a and 473c and the orientation of angled surfaces of cam followers 472b and 473b can be selected such that a certain degree of rotation of the articulation actuator 468 results in a predetermined degree of articulation of end effector 410. In at least one such embodiment, referring again to FIGS. 10 and 12, an approximately 180 degree rotation of actuator 468, and intermediate outer housing 462b, can result in an approximately 90 degree articulation of end effector 410. More particularly, in such circumstances, an approximately 180 degree rotation of actuator 468 can result in an approximately 45 degree articulation of intermediate outer housing 462b relative to proximal shaft portion 409a and, in addition, an approximately 45 degree articulation of distal shaft portion 409c and end effector 410 relative to intermediate outer housing 462b. Such circumstances can arise when cam surfaces 472a and 473c and cam follower surfaces 472b and 473b extend at approximately 22.5 degree angles with respect to longitudinal axis 499, for example. Other embodiments are envisioned in which a 180 degree rotation of actuator 468 results in less than or more than a 90 degree articulation of end effector 410. In various embodiments, the articulation angle defined between the unarticulated longitudinal axis 499 of proximal shaft portion 409a and the articulated longitudinal axis 499' of intermediate shaft portion 409b, i.e., first articulation angle 471, and the articulation angle defined between axis 499' and the articulated longitudinal axis 499" of distal shaft portion 409c, i.e., second articulation angle 475, can be the same, or at least substantially the same, when the end effector 410 is articulated. In other embodiments, the first articulation angle 471 and the second articulation angle 475 can be different. Such embodiments may be possible when the angle of first cam surface 472a is different than the angle of second cam surface 473c and/or when the angle of first cam follower surface 472b is different than the angle of second cam follower surface 473b, for example.

In various embodiments, the cam surfaces 472a and 473c and/or the cam follower surfaces 472b and 473b can be flat, or at least substantially flat wherein, as a result, the ratio between the rotation of articulation actuator 468 and the articulation of end effector 410 can be constant, or at least substantially constant, throughout the rotation of actuator 468 and the articulation of end effector 410. In certain embodiments, the ratio between the rotation of articulation actuator 468 and the articulation of end effector 410 can be variable, or non-constant, throughout the rotation of actuator 468 and the articulation of end effector 410. In at least one such embodiment, one or more of the cam surfaces 472a and 473c and/or one or more of the cam follower surfaces 472b and 473b can be curved, or arcuate, such that ratio between the rotation of actuator 468 and the articulation of end effector 410 is different at various points during the articulation of end effector 410. In certain embodiments, the ratio can be such that the end effector 410 articulates through a greater degree of articulation for a given degree of rotation of actuator during the initial rotation of actuator 468 and a lesser degree of articulation for the same given degree of rotation during the subsequent rotation of actuator 468, for example.

In various embodiments, further to the above, the shaft 408 and the end effector 410 can be configured such that the end effector 410 does not rotate, or at least substantially rotate, about its longitudinal axis when the end effector 410 is articulated. In at least one such embodiment, the longitudinal rotation of end effector 410 can be prevented, or at least substantially inhibited, by spine 464 rigidly mounted to distal shaft portion 409c and the presence of two articulation joints within the articulation joint 460. In embodiments having only one articulation axis within an articulation joint, such as articulation joint 360 (FIG. 7), for example, the articulation of the end effector may cause the end effector to rotate about its longitudinal axis which can invert, or at least partially invert, the end effector as it is articulated. In any event, the drive member of the shaft, such as drive member 366, for example, can be sufficiently flexible in order to accommodate the articulation within the articulation joint and, in certain embodiments, accommodate any twisting that may occur as a result of the inversion of the end effector. In certain embodiments, the cutting member, such as cutting member 340, for example, may comprise a bearing which can permit relative rotational movement between the drive member 366 and cutting member 340 and at least partially prevent torsional stress from building within the drive member 366. Drive member 466 and cutting member 440 (FIGS. 9 and 12) can comprise similar features. In various embodiments, the drive member 466 can be operably coupled with a trigger, such as trigger 128 (FIG. 1), for example, such that the actuation of trigger 128 can advance the drive member 466 and cutting member 440 between proximal and distal positions. In at least one such embodiment, the drive member 466 can comprise a cylindrical rod extending through the cavity 467 defined within the spine 464, wherein the outer diameter of drive member 466 can be closely received by the inner sidewalls of cavity 467. In various embodiments, the drive member 466 can be configured to slide within cavity 467 and, in at least one embodiment, can be supported laterally by the sidewalls of cavity 467.

In various embodiments, referring now to FIG. 14, an electrosurgical instrument can comprise an articulation joint, such as articulation joint 560, for example, which can pivotably connect an end effector 510 to a shaft 508. In use, referring now to FIG. 15, the end effector 510 can be articulated into a desired position and then clamped onto tissue by advancing cutting member 540 distally and moving first jaw 520A relative to second jaw 520B from an open position into a closed position. Alternatively, the first jaw 520A can be closed onto tissue by cutting member 540 before the end effector 510 is articulated. In either event, referring now to FIGS. 16 and 17, the end effector 510 can be moved between an unarticulated position (FIG. 16) and an articulated position (FIG. 17). As the end effector 510 is moved between its unarticulated and articulated positions, the end effector 510 can be moved through a range of positions therebetween. In certain embodiments, the shaft 508 and end effector 510 can be configured such that the end effector 510 can be removably locked into one or more pre-set positions. In at least one such embodiment, referring again to FIGS. 16 and 17, the shaft 508 can comprise one or more recesses or notches 562a-562c and the end effector 510 can comprise at least one detent or projection 564 which can be configured to be received within the notches 562a-562c. For example, when detent 564 is positioned in first notch 562a, the end effector 510 may be held in an articulated position to a first lateral side of longitudinal axis 599. In at least one such embodiment, the first notch 562a can comprise sidewalls which can be configured such that the detent 564 can abut the sidewalls and inhibit the detent 564 from being readily removed from the first notch 562a. In such embodiments, the end effector 510 may remain locked in position until a sufficient force or torque is applied to end effector 510 in order to push detent 564 out of first notch 562a and toward second notch 562b, for example. In certain embodiments, the surgical instrument can comprise an additional lock which can be slid distally into engagement with the end effector 510 in its articulated position and/or unarticulated position in order to further secure the end effector 510.

When detent 564 is sufficiently aligned with second notch 562b, further to the above, the detent 564 may be sufficiently positioned within the second notch 562b and the end effector 510 can be removably locked in an unarticulated position. Similar to first notch 562a, the sidewalls of the second notch 562b can be configured such that the detent 564 can abut the sidewalls which inhibit the detent 564 from being readily removed from the second notch 562b. Similarly, the end effector 510 may remain locked in position until a sufficient force or torque is applied to end effector 510 in order to push detent 564 out of second notch 562b and toward third notch 562c, for example. When detent 564 is sufficiently aligned with third notch 562c, the detent 564 may be sufficiently positioned within the third notch 562c and the end effector 510 can be removably locked in an articulated position to a second lateral side of longitudinal axis 599. Similar to second notch 562b, the sidewalls of the third notch 562c can be configured such that the detent 564 can abut the sidewalls which inhibit the detent 564 from being readily removed from the third notch 562c. Similarly, the end effector 510 may remain locked in position until a sufficient force or torque is applied to end effector 510 in order to push detent 564 out of third notch 562c. In various other embodiments, any suitable number of notches and/or detents, such as less than three notches or more than three notches, for example, can be utilized. In any event, the notches 562a-562c can be positioned circumferentially around a perimeter surrounding pivot 561 such that each notch is positioned the same distance, or at least substantially the same distance, from pivot 561. In at least one such embodiment, the shaft 508 can comprise a first set of notches 562a-562c around one end of pivot 561 and a second set of notches 562a-562c around the opposite end of pivot 561. Correspondingly, the end effector 510 can comprise a first detent 564 configured to engage the first set of notches 562a-562c and a second detent 564 configured to engage the second set of notches 562a-562c. In certain alternative embodiments, the shaft 508 can comprise a plurality of detents and the end effector can comprise at least one notch configured to selectively receive the detents.

In use, the end effector 510 may be inserted through a trocar, or other cannula, into a surgical site when the end effector 510 is in an unarticulated position. Once the end effector 510 has passed through the trocar, the end effector can be positioned against bone and/or tissue such that a longitudinal force can be transmitted through shaft 508 and end effector 510 along axis 599, or at least substantially along axis 599. In various circumstances, such a force can cause the end effector 510 to pivot or rotate relative to the shaft 508. As the end effector 510 is rotated, the detent 564 can snap-lock into one of the first recess 562a and 562c, for example, such that the end effector 510 is locked into an articulated position. In order to return the end effector 510 to an unarticulated position, the end effector 510 can be positioned against bone and/or tissue once again such that a torque can be generated between the shaft 508 and the end effector 510 in order to rotate the shaft 508 relative to the end effector 510. Once the end effector 510 has been returned to an unarticulated position, or an at least substantially unarticulated position, the end effector 510 can be pulled back through the trocar or cannula and removed from the surgical site. Various articulation joint arrangements are disclosed in United States Patent Application Publication No. 2007/0187453, entitled SURGICAL STAPLING AND CUTTING DEVICE, which was filed on Sep. 29, 2006; United States Patent Application Publication No. 2007/0073341, entitled METHOD FOR OPERATING A SURGICAL STAPLING AND CUTTING DEVICE, which was filed on Sep. 29, 2006; and United States Patent Application Publication No. 2007/0027469, entitled SURGICAL STAPLING AND CUTTING DEVICE AND METHOD FOR USING THE DEVICE, which was filed on Jul. 24, 2006, the entire disclosures of which are incorporated by reference herein. In various other embodiments, a surgical instrument can comprise an articulation actuator which can be configured to drive the end effector between unarticulated and articulated positions, including those described herein, for example.

Figure 20:
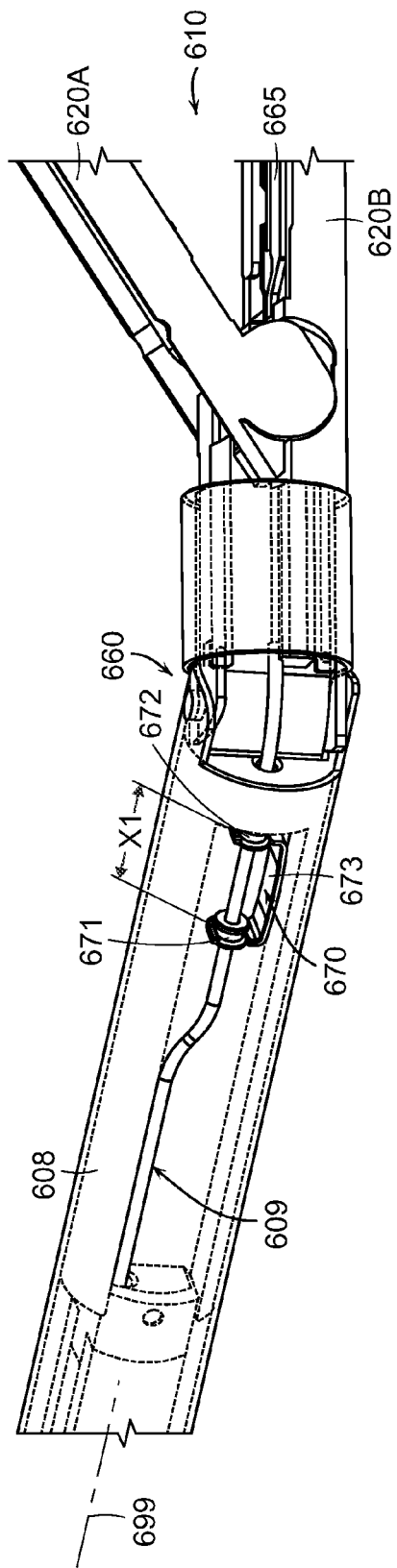
FIG. 20 is a perspective view of the end effector of FIG. 18 articulated to a second side.

Further to the above, referring now to FIGS. 18-20, an electrosurgical instrument can comprise a shaft 608, an end effector 610, and one or more electrodes, such as electrodes 665, for example, positioned within one or more of jaws 620A and 620B, for example, which can be configured to conduct electrical current. In various embodiments, the electrosurgical instrument can comprise one or more conductors, such as insulated wires, for example, which can electrically connect the electrodes 665 to an electrical source positioned within the handle of the surgical instrument and/or an electrical source operatively coupled with the handle, for example. In either event, the insulated wires, such as insulated wire 609, for example, can develop slack when the end effector 610 is articulated relative to the shaft 608 of the surgical instrument. In various circumstances, the slack generated within the wire 609 can cause the wire 609 to buckle, curl, and/or shift and, in some circumstances, interfere with the movement of end effector 610 relative to shaft 608. In various embodiments, the electrosurgical instrument can comprise a wire management system configured to manage to the slack in one or more insulated wires, for example. Referring now to FIG. 20, the end effector 610 is depicted as being articulated to a first side of longitudinal axis 699 and insulated wire 609 is depicted as having very little slack therein. As the end effector 610 is moved from its articulated position depicted in FIG. 20 to its unarticulated position illustrated in FIG. 19, slack can be created within the wire 609. In order to manage this slack such that it is accumulated, or at least substantially accumulated, in a desirable location, the surgical instrument can further comprise a wire tensioning device 670 which can be configured to draw slack within wire 609 into a location positioned proximally of articulation joint 660, for example.

In at least one embodiment, an insulated wire, such as wire 609, for example, can comprise a conductive core and an insulated jacket surrounding the conductive core. In various embodiments, further to the above, the wire tensioning device 670 can comprise a first, or proximal, end 671 which is attached to the insulation jacket of wire 609 and a second, or distal, end 672 which is also attached to the insulation jacket of wire 609. The first end 671 and the second end 672 can each be clamped to the wire 609 such that there is very little, if any, relative movement between the first end 671 and the wire 609 and, similarly, very little, if any, relative movement between the second end 672 and the wire 609. The wire tensioning device 670 can further comprise a spring member 673 connecting the first end 671 and the second end 672 which, in various embodiments, can be configured to bias the first end 671 and the second end 672 toward one another. In use, when the end effector 610 is in its maximum, or near maximum, articulated position illustrated in FIG. 20, the end effector 610 can apply a tensioning force to the wire 609 such that wire 609 is taut, or at least substantially taut, and the second, or distal, end 672 is pulled distally such that a maximum distance, or an at least near maximum distance, X1 is created between the first end 671 and the second end 672. As the end effector 610 is moved into its unarticulated position, illustrated in FIG. 19, slack can be created within the wire 609 and, owing to the resiliency of the spring portion 673 of wire tensioning device 670, the spring portion 673 can pull second end 672 and first end 671 toward one another such that a distance X2, which is shorter than distance X1, is defined between the first and second ends 671, 672. As a result of the above, as also illustrated in FIG. 19, slack within wire 609 can be accumulated between the first end 671 and the second end 672 and tension can be created within the remainder of wire 609 in order to keep wire 609 from accumulating, or at least substantially accumulating, within the articulation joint 660.

As the end effector 610 is moved into an articulated position on the opposite side of longitudinal axis 699, illustrated in FIG. 18, additional slack can be created within the wire 609. Owing to the resiliency of the spring portion 673 of wire tensioning device 670, the spring portion 673 can pull second end 672 and first end 671 of tensioning device 670 even closer to one another such that a distance X3, which is shorter than distance X2, is defined between the first and second ends 671, 672. In various circumstances, the position of the end effector in FIG. 18 can represent a maximum articulation to the opposite side of the longitudinal axis 699 and a fully-relaxed state of spring 673. In any event, as a result of the above, additional slack within wire 609 can be accumulated between the first end 671 and the second end 672 of tensioning device 670 and tension can be maintained within the remainder of wire 609 in order to keep wire 609 from accumulating, or at least substantially accumulating, within the articulation joint 660. When the end effector 610 is moved back toward its unarticulated position (FIG. 19), the end effector 610 can pull the wire 609 and stretch the tensioning device 670 by pulling the second end 672 distally relative to the first end 671. Similarly, when the end effector 610 is moved into the articulated position depicted in FIG. 20, the end effector 610 can pull the wire 609 once again and further stretch the tensioning device.

Figure 21:
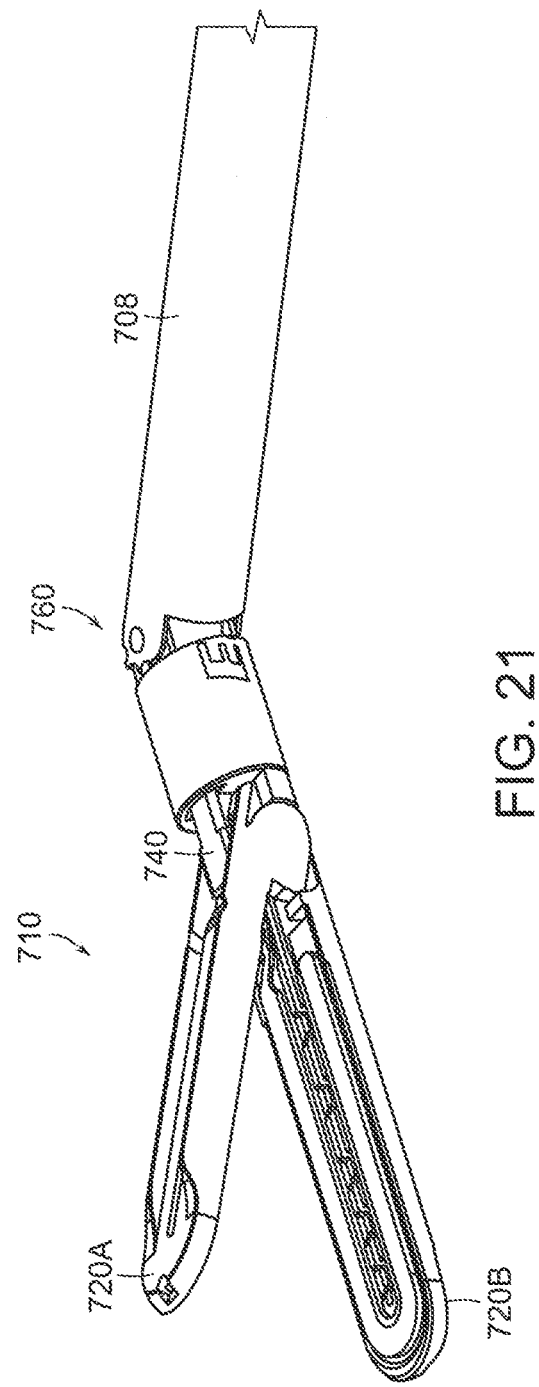
FIG. 21 is a perspective view of an end effector of an electrical surgical instrument, a distal end of a shaft, and an articulation joint connecting the end effector and the distal end of the shaft.
Figure 22:
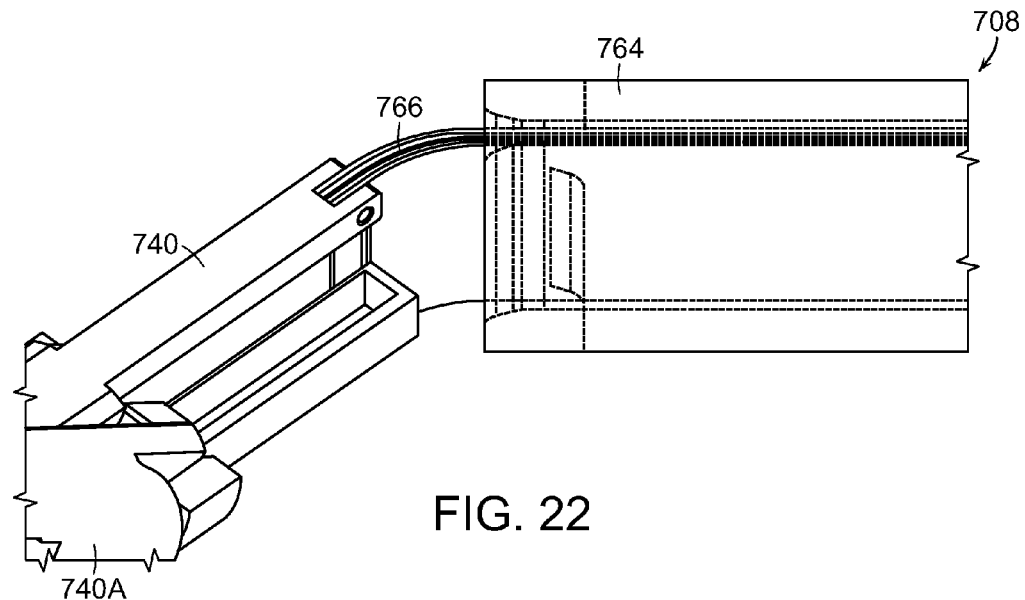
FIG. 22 is a perspective view of the articulation joint of FIG. 21 illustrated with some components removed.
Figure 23:
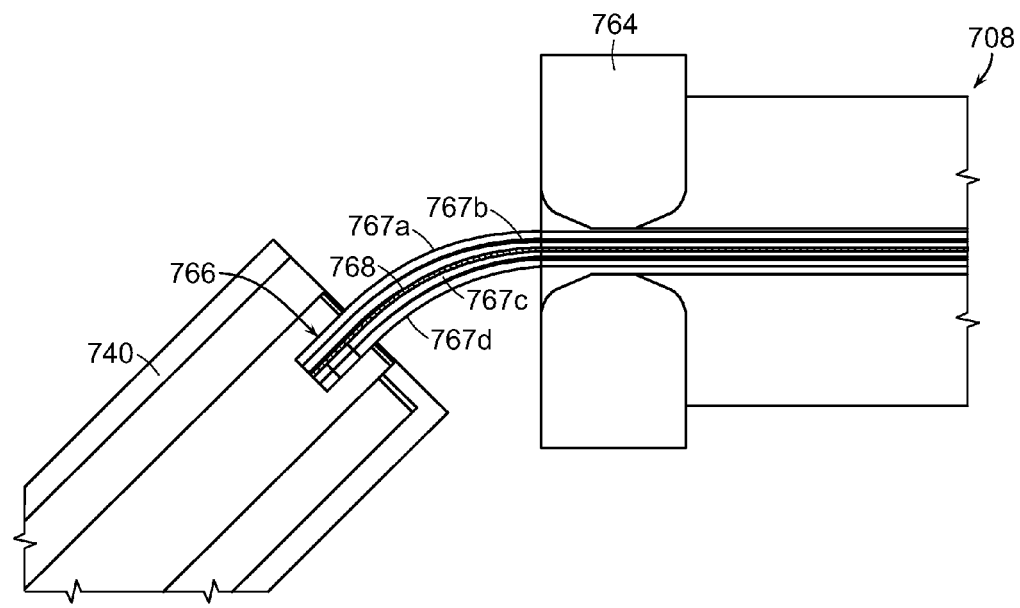
FIG. 23 is a top view of the articulation joint of FIG. 21 illustrated with some components removed.

In various embodiments, as described above, an electrosurgical instrument can comprise a drive member configured to advance a cutting member, for example, within an end effector of the electrosurgical instrument. In certain embodiments, referring now to FIGS. 21-23, an electrosurgical instrument can comprise a shaft 708, an end effector 710, and a drive member 766 operably coupled with a cutting member 740, wherein the distal displacement of drive member 766 and cutting member 740 is configured to move first jaw 720A toward second jaw 720B. In at least one such embodiment, the electrosurgical instrument can further comprise an articulation joint 760 which pivotably or rotatably connects the end effector 710 to shaft 708. Referring to FIGS. 22 and 23, the drive member 766 can comprise a plurality of flexible layers, or bands, such as flexible layers 767a-767d, for example, which can be configured to transmit a longitudinal load to cutting member 740 when the end effector 710 is in either an unarticulated position or an articulated position. In at least one such embodiment, the flexible layers of drive member 766 can be sufficiently flexible to bend within articulation joint 760 and accommodate the articulation of end effector 710. In various embodiments, the flexible layers 767a-767d of drive member 766 can slide or slip relative to one another. Such relative sliding or slipping between the layers 767a-767d can reduce resistance within the articulation joint 760. In certain embodiments, friction forces between adjacent flexible layers can at least partially resist the relative movement of the flexible layers. In certain alternative embodiments, the flexible layers can be adhered to one another by an adhesive to form a flexible laminate material. In various embodiments, at least one of the flexible layers, such as conductive layer 768, for example, can be comprised of a conductive material and can be configured to conduct electrical current through the drive member 766. Conductive layer 768 can be comprised of copper, brass, and/or a flexible conductive ribbon, for example. In at least one such embodiment, the conductive layer 768 can be positioned intermediate layer 767b and layer 767c which can be comprised of an insulative material, such as plastic, for example. In various embodiments, the conductive layer 768 can be in electrical communication with one or more electrodes positioned within the end effector 710 and, in addition, a power source positioned within, and/or operably coupled to, a handle of the surgical instrument. In at least one such embodiment, the cutting member 740 can be comprised of an electrically conductive material wherein the conductive layer 768 can be in electrical communication with one or more of the electrodes via the cutting member 740, for example. In various embodiments, conductive layer 768, and/or any other suitable layer, such as layers 767a-767d, for example, can be configured to, one, conduct current, and, two, transmit a longitudinal load or force therethrough. Similar to the above, conductive layer 768 can be configured to slide or slip relative to layers 767a-767d. In certain other embodiments, some layers can be configured to conduct current but may transmit little, if any, longitudinal load or force therethrough.

In various embodiments, the conductive layer 768 can be utilized to conduct current to the electrodes in lieu of an insulated wire, for example. In certain embodiments, a drive member can comprise more than one conductive layer. In at least one such embodiment, the drive member 766 can comprise one or more supply conductive layers, such as conductive layer 768, for example, and, in addition, one or more return conductive layers. More particularly, the drive member 766 can comprise a first conductive return layer positioned intermediate flexible layers 767a and 767b and a second conductive return layer positioned intermediate flexible layers 767c and 767d, for example. In at least one embodiment, the first and second return conductive layers can be comprised of a conductive material, such as copper and/or brass, for example, and the flexible layers 767a-767d can be comprised of an insulative material, such as plastic, for example. In at least one such embodiment, the supply conductive layer 768 can be in electrical communication with a power source, or positive voltage terminal of the power source, and one or more electrodes in end effector 710, as described above, wherein the return conductive layers can be in electrical communication with a ground, or negative voltage terminal of the power source, and one or more electrodes in end effector 710. In certain embodiments, the return conductive layers may not be in direct electrical communication with the electrodes; rather, they may be in contact with the tissue such that the current can flow from a supply electrode, through the tissue, and into the return conductive layers. In various embodiments, the supply flexible layers, the return flexible layers, and the insulative flexible layers may have the same, or at least substantially the same, width, height and length while, in certain other embodiments, such dimensions may be different between the layers.

Figure 24:
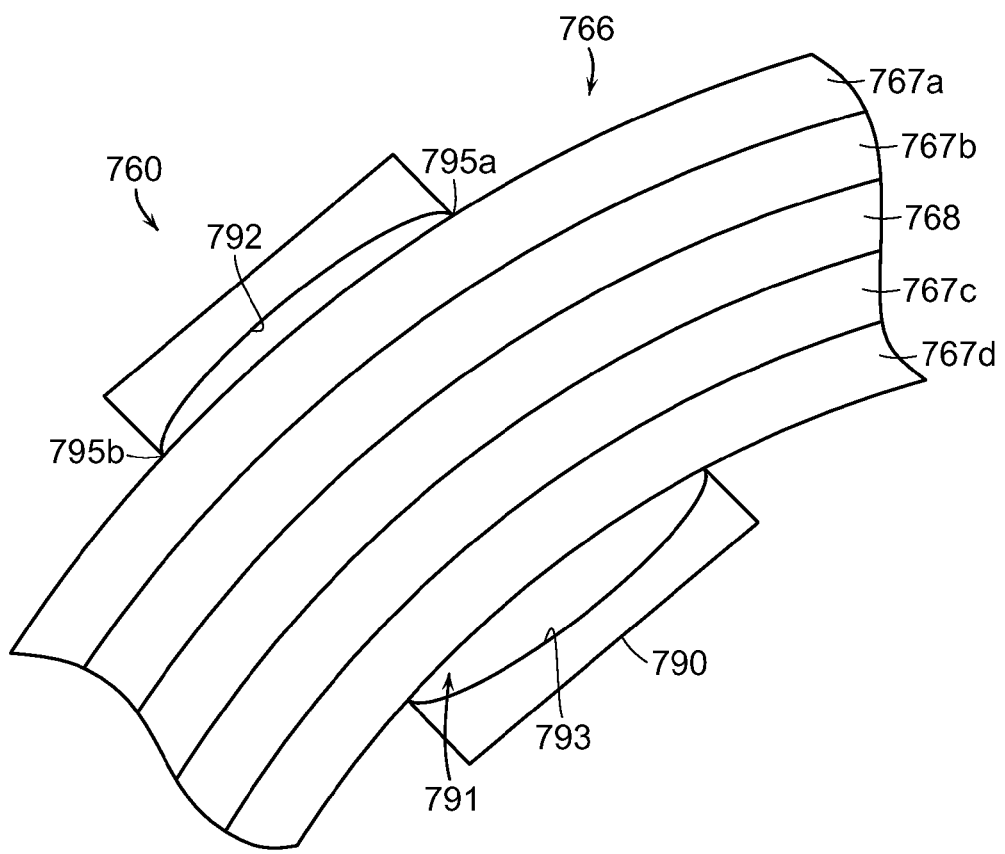
FIG. 24 is a top view of a support member engaged with a drive member extending through an articulation joint.

In various embodiments, further to the above, an electrosurgical instrument can further comprise a structure configured to prevent the flexible layers from buckling within the articulation joint. In at least one embodiment, referring now to FIG. 24, the electrosurgical instrument can comprise a structure 790 which can comprise a slot 791 configured to receive at least a portion of the drive member 766 therein. The slot 791 can be configured such that the drive member 766 can slide between the sidewalls 792 and 793 of slot 791 as the drive member 766 is advanced distally and/or retracted proximally. In use, the drive member 766 may bend within the articulation joint 760 wherein at least one of the sidewalls 792 and 793 can be configured to support the drive bar 766 when it is bent. In at least one embodiment, the first sidewall 792 and the second sidewall 793 can comprise concave surfaces against which the drive member 766 can be positioned. In at least one such embodiment, the sidewalls 792 and 793 can be defined by a radius of curvature which matches the smallest radius of curvature that is desired for the drive member 766. Stated another way, when the end effector 710 is only partially articulated, the radius of curvature which defines drive member 766 within the articulation joint 760 may be large and the possibility of drive member 766 buckling may be low. In such circumstances, referring to FIG. 24, the drive bar 766 may define a larger radius of curvature than the radius of curvature of sidewall 792 and/or sidewall 793 and, as a result, the drive bar 766 may contact the sidewall 792 and/or sidewall 793 at only a few locations, such as contact locations 795a and 795b, for example. In circumstances where the end effector 710 has been articulated to its maximum-articulated position, the radius of curvature which defines drive member 766 within the articulation joint 760 may be smaller and the possibility of drive member 766 buckling may be higher. Thus, in various embodiments, the radius of curvature of sidewalls 792 and 793 can be selected such that they match the smallest radius of curvature for drive member 766 that is desired. In such circumstances, the entirety, or at least substantial entirety, of sidewall 792 and/or sidewall 793 may be contacted by the drive member 766. In various circumstances, the first sidewall 792 may be configured to support the drive member 766 when the end effector 710 is articulated in a first direction and the second sidewall 793 may be configured to support the drive member 766 when the end effector 710 is articulated in a second, or opposite, direction. Various devices are disclosed in U.S. patent application Ser. No. 12/765,330, entitled SURGICAL STAPLING INSTRUMENT WITH AN ARTICULATABLE END EFFECTOR, which was filed on Apr. 22, 2010, the entire disclosure of which is incorporated by reference herein.

In various embodiments, referring now to FIGS. 25 and 26, an electrosurgical instrument can comprise an end effector 810, a shaft 808, and a drive member 840 which can be advanced distally in order to move first jaw 820A toward second jaw 820B. The shaft 808 can comprise an outer housing 862 which can also serve as an articulation driver 868. In certain embodiments, the articulation driver 868 can comprise a proximal end operably coupled with an articulation actuator located on the surgical instrument handle, for example. The articulation driver 868 can further comprise a distal end 867 which can define a circular, or at least substantially circular, ring of gear teeth extending around the perimeter of the distal end 867. In at least one embodiment, the gear teeth of distal end 867 can be meshingly engaged with the gear teeth of a gear member 869 mounted to end effector 810 such that the rotation of articulation driver 868 can be transmitted to end effector 810. More particularly, the gear teeth of distal end 867 and gear member 869 can be meshingly engaged such that, when the articulation driver 868 is rotated in a first direction 895 about longitudinal axis 899, the distal end 867 of driver 868 can drive the end effector 810 in a first direction 897 about pivot 861, as illustrated in FIG. 26, for example. Similarly, when the articulation driver 868 is rotated in the opposite direction, i.e., in a second direction 896, about longitudinal axis 899, the distal end 867 of driver 868 can drive the end effector 810 in an opposite direction, i.e., in a second direction 898, about pivot 861. In various embodiments, the gear member 869 can be fixedly mounted to the end effector 810 such that rotational movement of gear member 869 about pivot 861 is transmitted directly to the end effector 810.

In various embodiments, further to the above, the end effector 810 can comprise two gear members 869 fixedly mounted thereto which can be meshingly engaged with the gear teeth of distal end 867 of articulation driver 868. In at least one embodiment, the end effector 810 can comprise a first gear member 869 positioned at a first end of pivot 861 and a second gear member 869 positioned at a second, or opposite, end of pivot 861, for example. In at least one such embodiment, the articulation driver 868 can be configured to drive both gear members 869 simultaneously. In various embodiments, the shaft 808 can further comprise a spine member 864 extending through an aperture in outer housing 862. In use, the outer housing 862, or articulation driver 868, can be rotated about spine 864 in order to articulate end effector 810 as described above. The spine member 864 can comprise a proximal end which can be fixedly mounted to the handle of the surgical instrument and, in addition, a distal end which can comprise pivot mounts, or projections, 863 extending therefrom which can be positioned within pivot apertures in gear members 869. The pivot projections 863 can be closely received within the pivot apertures in gear members 869 and can define an axis about which the end effector 810 can be rotated.

In various embodiments, referring now to FIGS. 27-30, an electrosurgical instrument, such as surgical instrument 900, for example, can comprise a handle 905, a shaft 908 extending from the handle 905, and an end effector 910 rotatably coupled to the shaft 908 via an articulation joint 960. The handle 905 can comprise a trigger 928 which can be operably coupled with a drive member 966 such that an actuation of trigger 928 can move drive member 966 distally and advance a cutting member 940 within the end effector 910. In various embodiments, the articulation joint 960 can comprise an outer sheath 962, a cavity 963 defined by the outer sheath 962, and a plurality of spine members 964 extending inwardly into cavity 963. The drive member 966 can comprise an I-beam configuration, for example, which can include flanges 980 and a web 982 positioned intermediate flanges 980. In at least one embodiment, each spine member 964 can comprise a support surface 965 which can be configured to support the web 982 of drive member 966, for example, and prevent, or at least reduce the possibility of, the drive member 966 from becoming buckled. In at least one such embodiment, the support surfaces 965 can co-operatively define a slot 967 therein which can be configured to slidably receive and support the drive member 966. In certain embodiments, referring to FIG. 29, each spine member 964 can comprise a T-shaped configuration including a base member 984 and a support member 986 attached to the base member 984 which includes support surface 985. In at least one such embodiment, each spine member 964 may move independently of the others such that the spine members 964 do not inhibit, or at least substantially inhibit, the articulation of outer housing 962, for example. In certain embodiments, the base members 984 can be narrower than the support members 986 such that the spine members 986 may be flexible. In various embodiments, the spine members can comprise any other suitable shape or configuration, such as a U-shaped configuration, for example, wherein the bases of the U-shaped spine members can face inwardly toward the drive member 966, for example.

Figure 27:
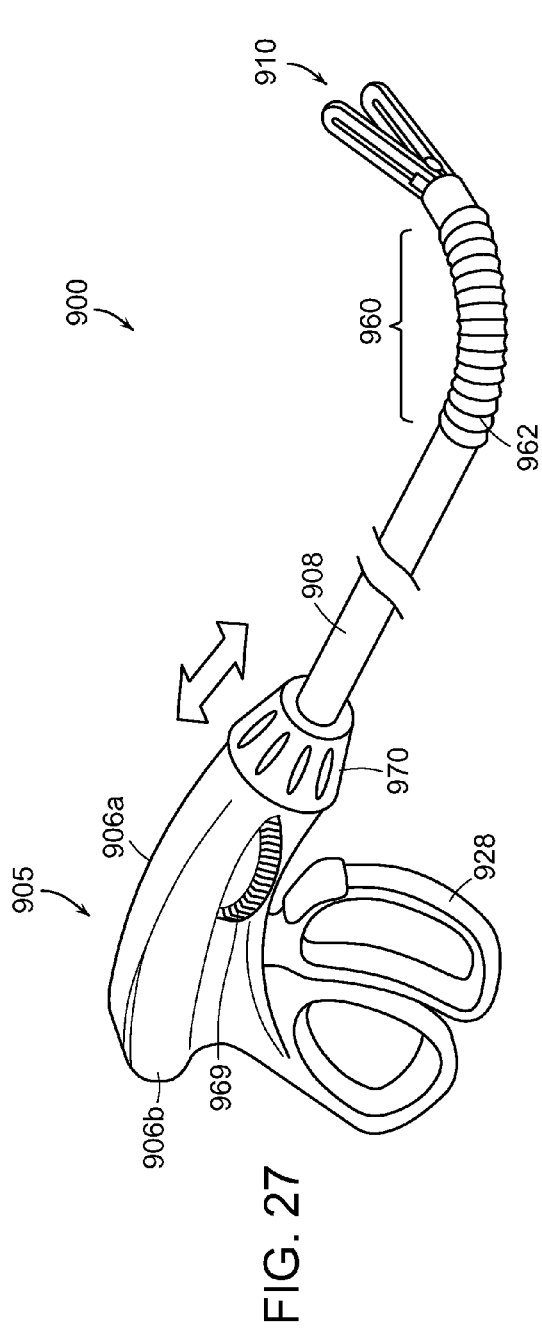
FIG. 27 is a perspective view of an electrosurgical instrument comprising a handle, a shaft extending from the handle, and an end effector configured to be articulated relative to the shaft by an actuator dial in the handle.
Figure 28:
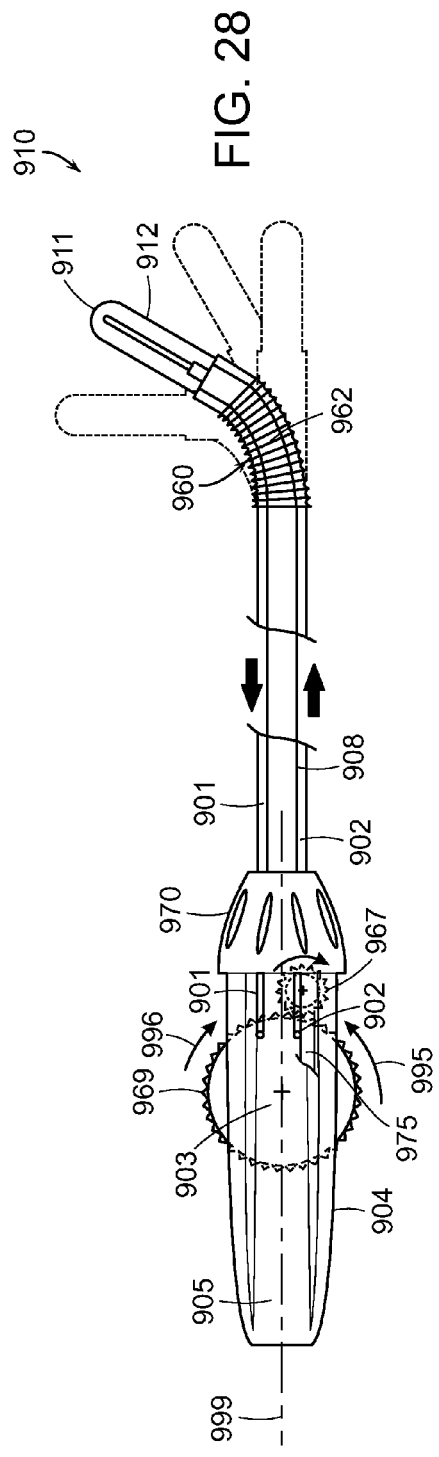
FIG. 28 is a top view of the electrosurgical instrument of FIG. 27.
Figure 30:
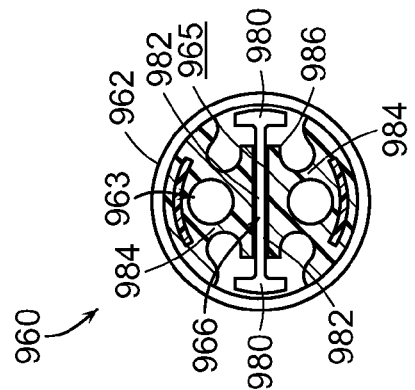
FIG. 30 is a cross-sectional end view of the articulation joint of the electrosurgical instrument of FIG. 27 taken along line 30-30 in FIG. 29.
Figure 29:
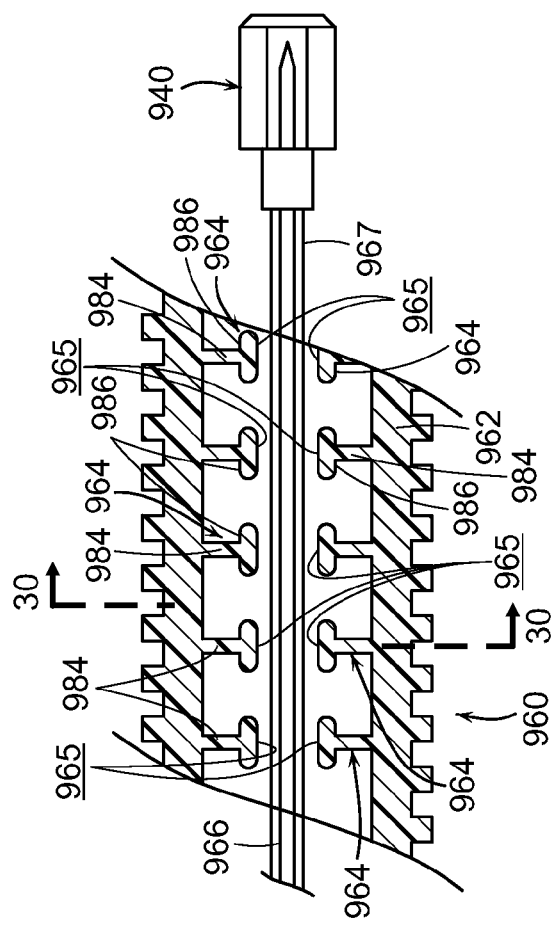
FIG. 29 is a partial cross-sectional view of an articulation joint connecting the shaft and the end effector of the electrosurgical instrument of FIG. 27.
Figure 31:
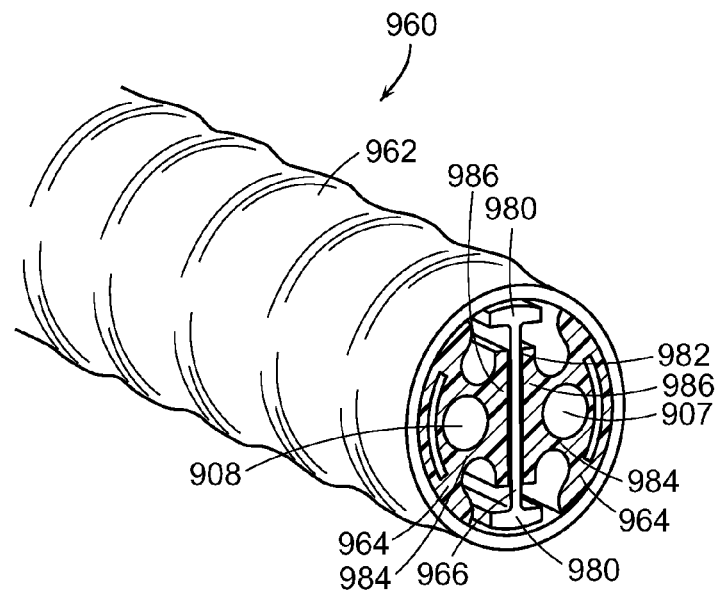
FIG. 31 is a cross-sectional perspective view of the articulation joint of the electrosurgical instrument of FIG. 27 in an unarticulated configuration.
Figure 32:
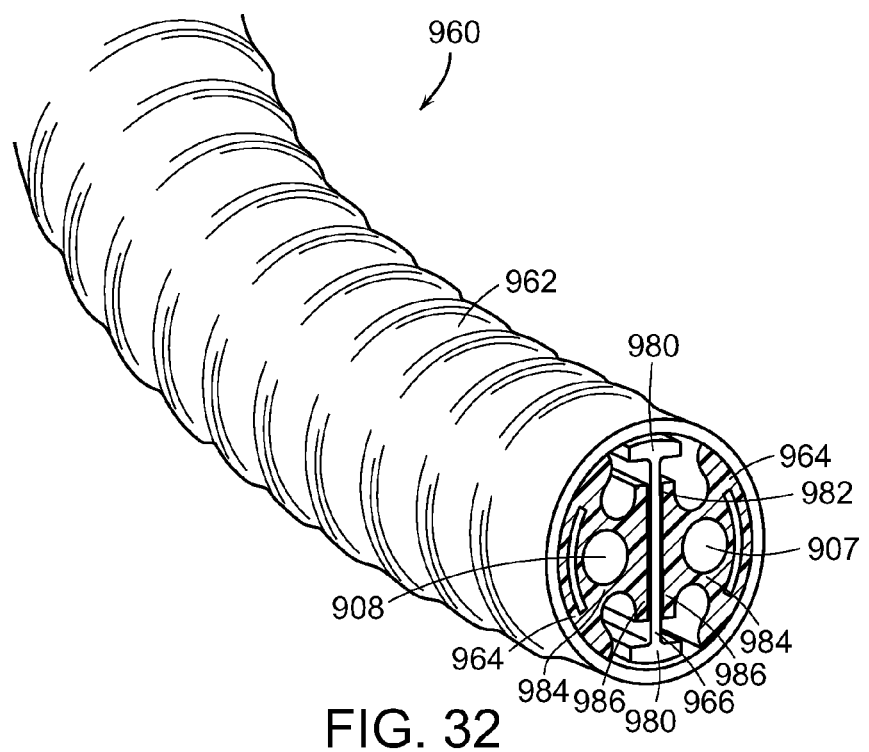
FIG. 32 is a cross-sectional perspective view of the articulation joint of the electrosurgical instrument of FIG. 27 in an articulated configuration.

In various embodiments, referring primarily to FIGS. 27 and 28, the handle 905 of the surgical instrument 900 can comprise an articulation actuator 969 which can be operably coupled with the end effector 910 such that the rotation of actuator 969 can articulate end effector 910. In at least one embodiment, referring primarily to FIGS. 28 and 31-35, the surgical instrument 900 can further comprise a first articulation driver 901 and a second articulation driver 902 wherein each of the articulation drivers 901 and 902 can be operably coupled to the articulation actuator 969 and the end effector 915. The first articulation driver 901 can have a proximal end attached to a first side 903 of the articulation actuator 969 and a distal end attached to a first side 911 of end effector 910, wherein the first side 903 of actuator 969 and the first side 911 of end effector 910 can be positioned on a first lateral side of longitudinal axis 999. In various embodiments, referring now to FIGS. 31, 32, 34, and 36, each spine member 964 can comprise an aperture 907 through which the first articulation driver 901 can extend. Similar to the above, the second articulation driver 902 can have a proximal end attached to a second side 904 of the articulation actuator 969 and a distal end attached to a second side 912 of end effector 910, wherein the second side 904 of actuator 969 and the second side 912 of end effector 910 can be positioned on a second lateral side of longitudinal axis 999. In various embodiments, referring again to FIGS. 31, 32, 34, and 36, each spine member 964 can comprise an aperture 908 through which the second articulation driver 902 can extend.

In use, further to the above, the articulation actuator 969 can be rotated in a first direction 995 in order to articulate end effector 910 to the first lateral side of longitudinal axis 999. More particularly, the first articulation driver 901 can be mounted to the articulation actuator 969 such that the rotation of actuator 969 in the first direction 995 can pull the first articulation driver 901 proximally and, as a result, pull the end effector 910 to the first lateral side. When the first articulation driver 901 is pulled proximally by the articulation actuator 969, the articulation actuator 969 can push the second articulation driver 902 distally which can, as a result, push the end effector 910 to the first lateral side. When the end effector 910 is articulated, in at least one such embodiment, the articulation joint 960 can bend along a radius of curvature instead of a single pivot axis. In at least one embodiment, the articulation joint 960 can be between approximately 1.0" and approximately 1.5" long, for example, and can be positioned approximately 0.2" to approximately 0.5", for example, proximally with respect to end effector 910. In at least one such embodiment, the length between the proximal end of the articulation joint 960 and the distal end of the end effector 910 can be between approximately 2.2" and approximately 3.0", for example. In any event, similar to the above, the articulation actuator 969 can be rotated in a second direction 996 in order to articulate end effector 910 to the second lateral side of longitudinal axis 999. More particularly, the second articulation driver 902 can be mounted to the articulation actuator 969 such that the rotation of actuator 969 in the second direction 996 can pull the second articulation driver 902 proximally and, as a result, pull the end effector 910 to the second lateral side. When the second articulation driver 902 is pulled proximally by the articulation actuator 969, the articulation actuator 969 can push the first articulation driver 901 distally which can, as a result, push the end effector 910 to the second lateral side. In various embodiments, the articulation actuator 969 can comprise a wheel which extends through a first slot in a first side 906a of the handle 905 and, in addition, a second slot in a second side 906b of the handle 905 which can permit the articulation actuator 969 to be rotated from the first side 906a and/or the second side 906b of the handle 905. In at least one such embodiment, the perimeter of the articulation actuator wheel can comprise serrations, and/or gear teeth, for example, which can allow the user of the surgical instrument to easily turn the articulation actuator 969.

In various embodiments, referring again to FIG. 28, the surgical instrument 900 can further comprise an articulation lock which can be configured to prevent the end effector 910 from being articulated. In at least one embodiment, although not illustrated, the handle 905 can comprise a lock which can be configured to directly engage the articulation actuator 969 in order to prevent, or at least substantially prevent, the articulation actuator 969 from rotating and thus preventing, or at least substantially preventing, the articulation actuator 969 from articulating end effector 910. In certain embodiments, referring again to FIG. 28, the handle 905 can comprise a lock gear 967 which can be meshingly engaged with gear teeth extending around the perimeter of articulation actuator 969. In at least one such embodiment, the handle 905 can comprise a lock 975 which can be selectively engaged with the lock gear 967 in order to prevent the lock gear 967 and the articulation actuator 969 from rotating. The handle 905 can further comprise a nozzle 970 which can be operably coupled with the lock 975 such that the lock 975 can be selectively engaged with and disengaged from the lock gear 967 by the movement of nozzle 970. More particularly, in at least one embodiment, the nozzle 970 can be retracted proximally in order to disengage the lock 975 from the lock gear 967 and moved distally in order to engage the lock 975 with the lock gear 967. In at least one such embodiment, the handle 905 can further comprise a biasing spring operably coupled with the nozzle 970 which can be configured to bias the lock 975 into engagement with the lock gear 967.

In use, the end effector 910 of the surgical instrument 900 can be inserted into a surgical site through a trocar, for example, in an unarticulated position. In various embodiments, the shaft 908 and end effector 910 can be selectively rotated about their longitudinal axis 999 in order to orient the end effector 910 in a desired orientation. More particularly, in at least one such embodiment, the user of the surgical instrument 900 can grasp nozzle 970, which can be keyed to the outer housing of shaft 908, and rotate nozzle 970 about longitudinal axis 999 in order to rotate shaft 908 and end effector 910. As outlined above, the user can pull the nozzle 970 proximally in order to disengage the articulation lock 975 from the articulation actuator 969 such that the articulation actuator 969 can be used to articulate the end effector 910 and/or such that the end effector 910 can be positioned against bone and/or tissue and forced to articulate relative to the shaft 908 by a force applied longitudinally through the shaft 908. In either event, once the end effector 910 has been suitably articulated, the nozzle 970 can be released in order to allow a spring or biasing member within the handle 905 to move nozzle 970 distally and re-engage the articulation lock 975 with the articulation actuator 969, for example. In order to treat the tissue, the trigger 928 can be actuated in order to advance drive member 966 and cutting member 940 distally and to close the end effector 910. As discussed above, the actuation of the trigger 928, and/or another trigger on handle 905, can be configured to operably connect a power source with electrodes in the end effector 910. In any event, after the cutting member 940 has been sufficiently advanced and the tissue has been sufficiently treated, the trigger 928 can be released and the drive member 966 and cutting member 940 can be retracted. Furthermore, the nozzle 970 can be retracted proximally once again in order to unlock the end effector 910 and allow the end effector 910 to be returned to an unarticulated position by rotating the articulation actuator 969 and/or pushing the end effector 910 against bone and/or tissue, for example. Once the end effector 910 has been sufficiently straightened, the end effector 910 can be withdrawn from the surgical site through the trocar.

Figure 37:
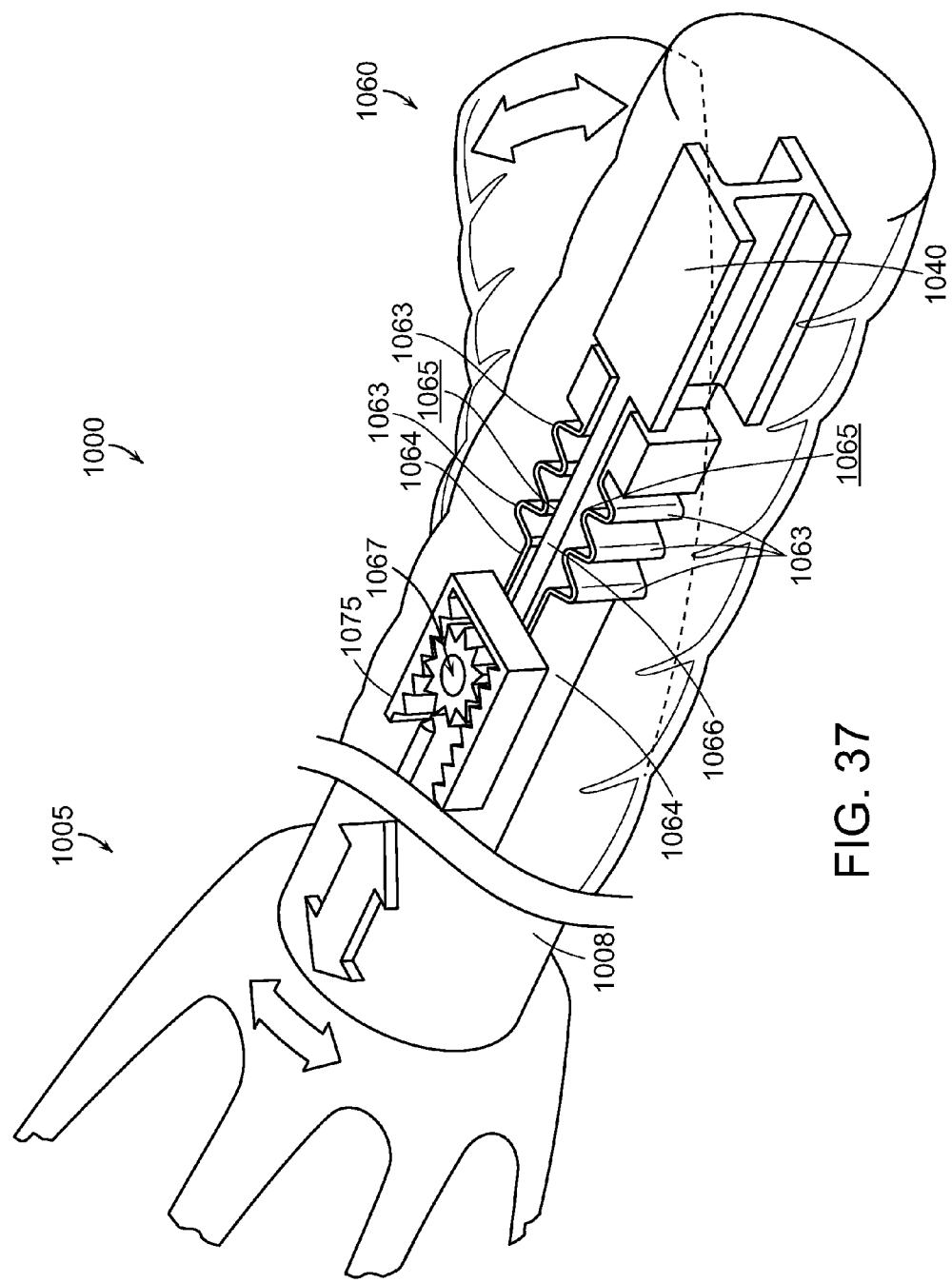
FIG. 37 is a perspective view of an articulation actuator of an electrosurgical instrument configured to articulate an end effector of the instrument.

In various embodiments, further to the above, a shaft and/or articulation joint of an electrosurgical instrument can further comprise one or more flexible rods extending through and mounted to an outer housing of the shaft which can be configured to, one, flexibly support the outer housing and, two, support a drive bar passing through the articulation joint. Such flexible rods, similar to the above, can comprise support surfaces configured to prevent, or at least reduce the possibility of, the drive member from becoming buckled. In various alternative embodiments, referring now to FIG. 37, a surgical instrument 1000, similar to surgical instrument 900, can comprise a handle 1005, a shaft 1008 extending from handle 1005, and an articulation joint 1060 connecting an end effector to the shaft 1008. Also similar to surgical instrument 900, surgical instrument 1000 can further comprise a drive bar 1066 extending through the articulation joint 1060, wherein the drive bar 1066 can be operably coupled with a cutting member 1040 and can be utilized to advance and/or retract the cutting member 1040 within the end effector. In various embodiments, the articulation joint 1060 can comprise support structures 1064 which can be configured to support the drive bar 1066 when the end effector is in an articulated position. The support structures 1064 can comprise a plurality of wave-shaped members 1063 which can each comprise a support surface 1065 configured to support the side of the drive bar 1066, for example. In various embodiments, the wave-shaped members 1063 can be configured to flex and stretch in order to accommodate the bending of articulation joint 1060 without inhibiting, or at least substantially inhibiting, the articulation of the end effector. In various embodiments, referring again to FIG. 37, the surgical instrument 1000 can further comprise an articulation lock member 1075 which can, similar to articulation lock member 975, be selectively engaged with an articulation gear 1067 in order to prevent the articulation gear 1067 from being rotated and the end effector from being articulated.

In various embodiments, referring now to FIGS. 38 and 39, a surgical instrument 1100 can comprise a handle 1105, a shaft 1108 extending from the handle 1105, and an end effector 1110 extending from the shaft 1108. The surgical instrument 1100 can further comprise an articulation joint 1160 positioned intermediate the shaft 1108 and the handle 1105 which can be configured to allow the handle 1105 to be articulated relative to the shaft 1108. In at least one such embodiment, the end effector 1110 and the shaft 1108 can be inserted through a trocar, for example, and into a surgical site such that at least a portion of the shaft 1108 and the articulation joint 1160 remains positioned externally to the trocar. In various embodiments, a trocar assembly can comprise a housing, a seal assembly, and a cannula which can define an aperture extending through the trocar assembly. One or more suitable trocars are disclosed in U.S. Pat. No. 7,371,227, entitled TROCAR SEAL ASSEMBLY, which issued on May 13, 2008, and U.S. Pat. No. 6,656,198, entitled TROCAR WITH REINFORCED OBTURATOR SHAFT, which issued on Dec. 2, 2003, the entire disclosures of which are hereby incorporated by reference herein. Other surgical site access devices are disclosed in U.S. Patent Application Publication No. 2010/0081995, entitled VARIABLE SURGICAL ACCESS DEVICE; U.S. Patent Application Publication No. 2010/0081883, entitled METHODS AND DEVICES FOR PERFORMING GASTROPLASTIES USING A MULTIPLE PORT ACCESS DEVICE; U.S. Patent Application Publication No. 2010/0081882, entitled MULTIPLE PORT SURGICAL ACCESS DEVICE; U.S. Patent Application Publication No. 2010/0081881, entitled SURGICAL ACCESS DEVICE WITH PROTECTIVE ELEMENT; U.S. Patent Application Publication No. 2010/0081880, entitled SURGICAL ACCESS DEVICE; U.S. Patent Application Publication No. 2010/0081864, entitled METHODS AND DEVICES FOR PERFORMING GASTRECTOMIES AND GASTROPLASTIES; U.S. Patent Application Publication No. 2010/0081863, entitled METHODS AND DEVICES FOR PERFORMING GASTRECTOMIES AND GASTROPLASTIES, the entire disclosures of which are incorporated by reference herein. Several of these devices can comprise single-site access devices which can permit the insertion of multiple laparoscopic instruments, for example, through several apertures in the same access device. In at least one embodiment, such a single-site access device can be inserted through an incision in the umbilicus, for example.

In various circumstances, as outlined above, several surgical instruments can be inserted into a surgical site through the same access device. In such circumstances, among others, the handles of these surgical instruments can be positioned adjacent to one another thereby increasing the difficulty of accessing and using the surgical instruments. In order to position the handle 1105 in a more desirable position to actuate trigger 1128, the handle 1105 can be rotated or pivoted relative to the shaft 1108. In at least one embodiment, the articulation joint 1160 can comprise a ball and socket joint including ball 1161 mounted to the proximal end of shaft 1108 and socket 1162 in the distal end of handle 1105 which can allow the handle 1105 to be rotated relative to the shaft 1108 about more than one axis. More particularly, the ball and socket joint can be configured to permit handle 1105 to be rotated about longitudinal axis 1199 as indicated by arrow 1196 and/or one or more axes, such as axes 1197 and 1198, for example, which are perpendicular to longitudinal axis 1199. Such rotation is depicted by arrows 1194 and 1195, for example. In various embodiments, the socket 1162 can be configured to surround a sufficient portion of the ball 1161 so as to prevent the ball 1161 from being removed from the socket 1162 during use. In at lest one such embodiment, the socket 1162 can surround over half the perimeter of ball 1161. Various articulation joints are contemplated which can permit the handle of the surgical instrument to articulate relative to the shaft of the surgical instrument including those disclosed in U.S. Patent Application Publication No. 2007/0179476, entitled ENDOSCOPIC SURGICAL INSTRUMENT WITH A HANDLE THAT CAN ARTICULATE WITH RESPECT TO THE SHAFT, the entire disclosure of which is incorporated by reference herein, for example. In any event, in various embodiments, the handle 1105 can be rotated between a position which lies along longitudinal axis 1199 of shaft 1108 to a position which is off-axis with respect to axis 1199. Once articulated, the trigger 1128, for example, can be actuated to advance at least one of a closure member configured to close the end effector 1110 and/or advance a firing member distally in order to incise tissue, for example. Such a closure member and/or firing member can be sufficiently flexible in order to accommodate the articulation of joint 1160. In various embodiments, the firing member can comprise a plurality of flexible layers which can slide relative to one another. In certain embodiments, the firing member can have a circular, or an at least generally circular, cross-section, for example, and, in at least one embodiment, the firing members can comprise layers having a taller height in the middle of the cross-section and layers having a shorter height at the sides of the cross-section, for example. Firing members having a circular, or an at least generally circular, cross-section, can facilitate the selective articulation of handle 1105 about axes 1197 and 1198 and/or any other suitable axis. The entire disclosure of United States Patent Application Publication No. 2007/0208312, entitled APPARATUS AND METHOD FOR MINIMALLY INVASIVE SURGERY, is hereby incorporated by reference herein. The entire disclosure of U.S. patent application Ser. No. 12/775,724, entitled COMPOUND ANGLED LAPARASCOPIC METHODS AND DEVICES, which was filed on May 7, 2010, is hereby incorporated by reference herein.

In various embodiments, as described above, current can flow from one electrode to another while passing through the tissue captured by the end effector of the surgical instrument. As also described above, the current passing through the tissue can heat the tissue. In various circumstances, however, the tissue may become overheated. In order to avoid such overheating, the electrodes of various surgical instruments can comprise materials which may no longer conduct current, or may conduct at least substantially less current, when the electrode materials have reached or exceeded a certain temperature. Stated another way, in at least one embodiment, the electrical resistance of the electrode material can increase with the temperature of the material and, in certain embodiments, the electrical resistance of the material can increase significantly when the material has reached or exceeded a certain transition, or switching, temperature. In various circumstances, such materials can be referred to as positive temperature coefficient, or PTC, materials. In at least some such PTC materials, the PTC material can be comprised of a first non-conductive material, or substrate, which has a high electrical resistance and, in addition, a second, conductive material, or particles, having a lower electrical resistance interdispersed throughout the substrate material. In at least one embodiment, the substrate material can comprise polyethylene and/or high-density polyethylene (HDPE), for example, and the conductive material can comprise carbon particles, for example. In any event, when the temperature of the PTC material is below its transition temperature, the conductive material can be present in the non-conductive material in a sufficient volumetric density such that the current can flow through the PTC material via the conductive particles. When the temperature of the PTC material has exceeded its transition temperature, the substrate, or non-conductive material may have sufficiently expanded and/or changed states such that the conductive particles are no longer sufficiently in contact with one another in order provide a sufficient path for the current to flow therethrough. Stated another way, the expansion and/or state change of the substrate material may cause the volumetric density of the conductive particles to fall below a sufficient volumetric density in order for current to be conducted therethrough, or at least substantially conducted therethrough. In various circumstances, as a result of the above, the PTC material may act as a circuit breaker which can prevent, or at least inhibit, additional energy from reaching the tissue being treated, that is, at least until the PTC material has cooled sufficiently and reached a temperature which is below the transition, or switching, temperature. At such point, the PTC material could begin to conduct current again.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments.

However, surgical instruments may be used in many orientations and positions, and these terms are not intended to be limiting and absolute.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a handle;
   a trigger;
   an articulation actuator;
   an end effector, comprising:
      a first jaw member;
      a second jaw member, wherein one of said first jaw member and said second jaw member is movable relative to the other of said first jaw member and said second jaw member; and
      an electrode;
   a power switch selectively actuatable to operably couple said electrode with a power source; and
   a shaft extending between said handle and said end effector, wherein said shaft comprises:
      an outer tube, comprising:
         a first portion comprising a proximal end mounted to said handle and a distal end comprising a first angled surface;
         a second portion comprising a distal end mounted to said end effector and a proximal end comprising a second angled surface, wherein said second portion is rotatable relative to said first portion; and
         an inner cavity extending through said first portion and said second portion;
      a drive member extending through said inner cavity, wherein said drive member is operably coupled to said trigger, wherein an actuation of said trigger is configured to move said drive member from a proximal position to a distal position; and
      an articulation member extending through said inner cavity, wherein said articulation member is rotatable relative to said first portion of said outer tube, wherein said articulation member is operably mounted to said articulation actuator and said second portion of said outer tube such that the rotation of said articulation actuator is configured to rotate said second portion relative to said first portion, wherein said second angled surface is configured to contact said first angled surface when said second portion is rotated relative to said first portion on a rotation axis in order to articulate said second portion on an articulation axis relative to said first portion, and wherein said articulation axis is different than said rotation axis.

2. The surgical instrument of claim 1, wherein said first angled surface is parallel to said second angled surface.

3. The surgical instrument of claim 1, wherein said shaft defines a longitudinal axis, and wherein said first angled surface and said second angled surface extend transversely to said longitudinal axis.

4. The surgical instrument of claim 1, wherein said drive member is configured to move said first jaw between an open position and a closed position as said drive member is moved from said proximal position to said distal position.

5. The surgical instrument of claim 1, wherein said articulation member comprises a tube extending through said inner cavity of said outer tube, wherein said tube of said articulation member comprises a second inner cavity, and wherein said drive member extends through said second inner cavity.

6. The surgical instrument of claim 1, wherein said outer tube defines a longitudinal axis extending through said first portion and said second portion of said outer tube when said second portion is unarticulated relative to said first portion, wherein said articulation member is positioned concentrically along said longitudinal axis, and wherein said second portion is configured to articulate relative to said first portion when said second portion is rotated about said longitudinal axis.

7. The surgical instrument of claim 1, wherein said articulation member is configured to inhibit said second portion of said outer tube from moving distally relative to said first portion of said outer tube.

8. The surgical instrument of claim 1, further comprising a biasing member operably engaged with at least one of said articulation actuator and said articulation member, wherein said biasing member is configured to apply a biasing force to said first portion of said outer tube and bias said first angled surface against said second angled surface.

9. The surgical instrument of claim 1, wherein said outer tube defines a longitudinal axis extending through said first portion and said second portion of said outer tube when said second portion is unarticulated relative to said first portion, wherein said second portion of said outer tube is configured to be rotated about said longitudinal axis by said articulation member, wherein said first angled surface comprises a cam, wherein said second angled surface comprises a cam follower, and wherein said cam is configured to rotate said cam follower about an axis which is perpendicular to said longitudinal axis.

10. A surgical instrument, comprising:
    a handle;
    a trigger;
    an articulation actuator;
    an end effector, comprising:
       a first jaw member;
       a second jaw member, wherein one of said first jaw member and said second jaw member is movable relative to the other of said first jaw member and said second jaw member; and
       an electrode;
    a power actuator selectively actuatable to operably couple said electrode with a power source; and
    a shaft extending between said handle and said end effector, wherein said shaft comprises:
       an outer tube, comprising:
          a first portion comprising a proximal end mounted to said handle and a distal end comprising a first cam surface;

a second portion comprising a distal end mounted to said end effector and a proximal end comprising a second cam surface;

an intermediate portion positioned intermediate said first portion and said second portion, wherein said intermediate portion is rotatable relative to said first portion and said second portion, and wherein said intermediate portion comprises:

a first cam follower surface positioned opposite said first cam surface; and a second cam follower surface positioned opposite said second cam surface; and an inner cavity extending through said first portion, said intermediate portion, and said second portion;

a spine extending through said inner cavity, wherein said spine is mounted to at least one of said end effector and said second portion of said outer tube and at least one of said handle and said first portion of said outer tube;

a drive member extending through said inner cavity, wherein said drive member is operably coupled to said trigger, wherein an actuation of said trigger is configured to move said drive member from a proximal position to a distal position; and an articulation member extending through said inner cavity, wherein said articulation member is rotatable relative to said first portion of said outer tube, wherein said articulation member is operably mounted to said articulation actuator and said intermediate portion of said outer tube such that the rotation of said articulation actuator is configured to rotate said intermediate portion relative to said first portion, wherein said first cam follower surface is configured to contact said first cam surface when said intermediate portion is rotated relative to said first portion on a rotation axis in order to articulate said intermediate portion relative to said first portion on an articulation axis, and wherein said articulation axis is different than said rotation axis.

11. The surgical instrument of claim 10, wherein the rotation of said articulation actuator is configured to rotate said intermediate portion relative to said second portion, and wherein said second cam follower surface is configured to contact said second cam surface when said intermediate portion is rotated relative to said second portion in order to articulate said second portion relative to said intermediate portion.

12. The surgical instrument of claim 10, wherein said outer tube defines a longitudinal axis extending through said first portion, said intermediate portion, and said second portion of said outer tube when said intermediate portion and said second portion are unarticulated relative to said first portion, wherein said first cam surface comprises a first angled surface, wherein said second cam surface comprises a second angled surface, and wherein said first angled surface and said second angled surface extend transversely to said longitudinal axis.

13. The surgical instrument of claim 12, wherein said second portion of said outer tube is configured to be rotated about said longitudinal axis by said articulation member, wherein said first angled surface comprises a cam, wherein said second angled surface comprises a cam follower, and wherein said cam is configured to rotate said cam follower about an axis which is perpendicular to said longitudinal axis.

14. The surgical instrument of claim 10, wherein said drive member is configured to move said first jaw between an open position and a closed position as said drive member is moved from said proximal position to said distal position.

15. The surgical instrument of claim 10, wherein said articulation member comprises a tube extending through said inner cavity of said outer tube, wherein said tube of said articulation member comprises a second inner cavity, and wherein said drive member and said spine extend through said second inner cavity.

16. The surgical instrument of claim 10, wherein said outer tube defines a longitudinal axis extending through said first portion, said intermediate portion, and said second portion of said outer tube when said intermediate portion and said second portion are unarticulated relative to said first portion, wherein said articulation member is positioned concentrically along said longitudinal axis, and wherein said intermediate portion is configured to articulate relative to said first portion when said intermediate portion is rotated about said longitudinal axis.

17. The surgical instrument of claim 10, wherein said spine member is configured to inhibit said second portion of said outer tube from rotating relative to said first portion.

18. The surgical instrument of claim 10, wherein said outer tube defines a longitudinal axis extending through said first portion, said intermediate portion, and said second portion of said outer tube when said intermediate portion and said second portion are unarticulated relative to said first portion, wherein said intermediate portion of said outer tube is configured to be rotated about said longitudinal axis by said articulation member, and wherein said first cam surface is configured to rotate said first cam follower surface about an axis which is perpendicular to said longitudinal axis.

19. A surgical instrument, comprising:

a handle;

an articulation actuator;

an end effector; and a shaft extending between said handle and said end effector, wherein said shaft comprises:

an outer tube, comprising:

a first portion comprising a proximal end mounted to said handle and a distal end comprising a first cam surface;

a second portion comprising a distal end mounted to said end effector and a proximal end comprising a second cam surface;

an intermediate portion positioned intermediate said first portion and said second portion, wherein said intermediate portion is rotatable relative to said first portion and said second portion, and wherein said intermediate portion comprises:

a first cam follower surface positioned opposite said first cam surface; and a second cam follower surface positioned opposite said second cam surface; and an inner cavity extending through said first portion, said intermediate portion, and said second portion;

a spine extending through said inner cavity, wherein said spine is mounted to at least one of said end effector and said second portion of said outer tube and at least one of said handle and said first portion of said outer tube; and an articulation member extending through said inner cavity, wherein said articulation member is rotatable relative to said first portion of said outer tube, wherein said articulation member is operably mounted to said articulation actuator and said intermediate portion of said outer tube such that the rotation of said articulation actuator is configured to rotate said intermediate portion relative to said first portion, wherein said first cam follower surface is configured to contact said first cam surface when said intermediate portion is rotated relative to said first portion on a rotation axis in order to articulate said intermediate portion relative to said first portion on an articulation axis, and wherein said articulation axis is different than said rotation axis.

* * * * *